US009446112B2

(12) United States Patent
Kutzler et al.

(10) Patent No.: US 9,446,112 B2
(45) Date of Patent: Sep. 20, 2016

(54) CLOSTRIDIUM DIFFICILE DNA VACCINE

(75) Inventors: Michele Kutzler, Souderton, PA (US);
Scott Baliban, Southampton, NJ (US);
David B. Weiner, Merion, PA (US);
Niranjan Y. Sardesai, Blue Bell, PA (US); J. Joseph Kim, Harleyville, PA (US)

(73) Assignees: Philadelphia Health & Education Corporation, Philadelphia, PA (US);
Inovio Pharmaceuticals, Inc., Plymouth Meeting, PA (US); The Trustees of the University of Pennsylvania, Philadelphia, PA (US)

( * ) Notice: Subject to any disclaimer, the term of this patent is extended or adjusted under 35 U.S.C. 154(b) by 255 days.

(21) Appl. No.: 14/232,048

(22) PCT Filed: Jul. 12, 2012

(86) PCT No.: PCT/US2012/046422
§ 371 (c)(1),
(2), (4) Date: Jul. 14, 2014

(87) PCT Pub. No.: WO2013/055420
PCT Pub. Date: Apr. 18, 2013

(65) Prior Publication Data
US 2014/0341936 A1 Nov. 20, 2014

Related U.S. Application Data

(60) Provisional application No. 61/506,973, filed on Jul. 12, 2011.

(51) Int. Cl.
| | |
|---|---|
| *C07H 21/04* | (2006.01) |
| *A61K 39/00* | (2006.01) |
| *A61K 39/08* | (2006.01) |
| *A61N 1/32* | (2006.01) |
| *C07K 14/33* | (2006.01) |

(52) U.S. Cl.
CPC .............. *A61K 39/08* (2013.01); *A61N 1/327* (2013.01); *C07K 14/33* (2013.01); *A61K 2039/53* (2013.01)

(58) Field of Classification Search
CPC ........................................................ A61K 39/08
USPC ....................................................... 536/23.7
See application file for complete search history.

(56) References Cited

U.S. PATENT DOCUMENTS

| 6,733,994 B2 | 5/2004 | Weiner et al. |
| 7,625,559 B2 | 12/2009 | Ambrosino et al. |

FOREIGN PATENT DOCUMENTS

| JP | 2004510440 A | 4/2004 |
| JP | 2007533330 A | 11/2007 |
| WO | 0229088 A2 | 4/2002 |
| WO | 2006121422 A2 | 11/2006 |
| WO | 2007/146139 | 12/2007 |
| WO | 2011/060431 | 5/2011 |

OTHER PUBLICATIONS

Gardiner (Vaccine, 2009, 27:3598-3604).*
Baliban Scott M et al., "Development of a Novel DNA Vaccine Strategy for Prevention of Clostridium difficile Infection," *Molecular Therapy*, 2012, vol. 20, No. Suppl. 1.
Baliban Scott M et al., "An Optimized Synthetic DNa Vaccine Encoding the Toxin A and Toxin B Receptor Binding Domains of Clostridium difficile Induces Protective Antibody Responses In Vivo," *Infection and Immunity, American Society for Microbiology*, 2014, vol. 82, No. 10.
Javier F. Torres et al., "Evaluation of Formalin-Inactivated *Clostridium difficile* Vaccines Administered by Parenteral and Mucosal Routes of Immunization of Hamsters," *Infection and Immunity*, 1995, 63(12):4619-4627.
Michele A. Kutzler et al., "Coimmunization with an Optimized IL-15 Plasmid Results in Enhanced Function and Longevity of CD8 T Cells that are Partially Independent of CD4 T Cell Help," *J Immunol*, 2005, 175:112-123.
Daniel E. Voth et al., "*Clostridium difficile* Toxins: Mechanism of Action and Role in Disease," *Clin. Microbiol.*, 2005, 18(2):247-263.
Chandrabali Ghose et al., "Transcutaneous Immunization with *Clostridium difficile* Toxoid A Induces Systemic and Mucosal Immune Responses an Toxin A-Neutralizing Antibodies in Mice," *Infection and Immunity*, 2007, 75(6):2826-2832.
Dominick J. Laddy et al., "Heterosubtypic Protection against Pathogenic Human and Avian Influenza Viruses via In Vivo Electroporation of Synthetic Consensus DNA Antigens," *PLoS One*, 2008, 3(6):e2517, pp. 1-8.
Déirdre B. Ní Eidhin et al., "Active immunization of hamsters against *Clostridium difficile* infection using surface-layer protein," *FEMS Immunol Med Microbiol*, 2008, 52:207-218.
Claribel P. Taylor et al., "Open-Label, Dose Escalation Phase I Study in Healthy Volunteers to Evaluate the Safety and Pharmacokinetics of a Human Monoclonal Antibody to *Clostridium difficile* Toxin A," *Vaccine*, 2008, 26(27-28):3404-3409.
David F. Gardiner et al., "A DNA vaccine targeting the receptor-binding domain of *Clostridium difficile* toxin A," *Vaccine*, 2009, 27(27):3598-3604.
Jiangmei Yin et al., "High dose of plasmid IL-15 inhibits immune responses in an influenze non-human primates immunogenicity model," *Virology*, 2009, 393:49-55.
Brett A. Leav et al., "Serum anti-toxin B antibody correlates with protection from recurrent *Clostridium difficile* infection (CDI)," *Vaccine*, 2010, 28:965-969.
Lauren A. Hirao et al., "Multivalent Smallpox DNA Vaccine Delivered by Intradermal Electroporation Drives Protective Immunity in Nonhuman Primates Against Lethal Monkeypox Challenge," *The Journal of Infectious Diseases*, 2011, 203:95-102.

(Continued)

*Primary Examiner* — Valarie Bertoglio
(74) *Attorney, Agent, or Firm* — Rivers de Law LLP

(57) ABSTRACT

The invention relates to compositions and methods for treating *C. difficile* associated disease (CDAD) through the administration to a subject in need thereof at least one nucleic acid encoding at least a portion of at least one of toxin A and toxin B.

8 Claims, 22 Drawing Sheets

(56) References Cited

OTHER PUBLICATIONS

Karthik Mallilankaraman et al., "A DNA Vaccine against Chikungunya Virus is Protective in Mice and Includes Neutralizing Antibodies in Mice and Nonhuman Primates," *PLoS Negl Trop Dis*, 2011, 5(1):e928.
Matthias A. Oberli et al., "A Possible Oligosaccharide-Conjugate Vaccine Candidate for *Clostridium difficile* Is Antigenic and Immunogenic," *Chemistry & Biology*, 2011, 18:580-588.
Séverine Péchiné et al., "Immunization of hamsters against *Clostridium difficile* infection using the Cwp84 protease as an antigen," *FEMS Immunol Med Microbiol*, 2011, 63:73-81.
Patima Permpoonpattana et al., "Immunization with *Bacillus* spores Expressing Toxin A Peptide Repeats Protects against Infection with *Clostridium difficile* Strains Producing Toxins A and B," *Infection and Immunity*, 2011, 79(6):2295-2302.
Saima Aslam et al., "Treatment of *Clostridium difficile*-associated disease: old therapies and new strategies," *Lancet Infect Dis*, 2005, 5:549-557.
Siew-Yen Chong et al., "Comparative ability of plasmid IL-12 and IL-15 to enhance cellular and humoral immune responses elicited by a SIV gag plasmid DNA vaccine and alter disease progression following SHIV$_{89.6P}$ challenge in rhesus macaques," *Vaccine*, 2007, 25:4967-4982.
David A. Hokey et al., "DNA vaccines for HIV: challenges and opportunities," *Springer Semin Immun*, 2006, 28:267-279.
Kimberly A. Kraynyak et al., "Systemic immunization with CCL27/CTACK modulates immune responses at mucosal sites in mice and macaques," *Vaccine*, 2010, 28:1942-1951.
Ma Kutzler et al., "Plasmids encoding the mucosal chemokines CCL27 and CCL28 are effective adjuvants in eliciting antigen-specific immunity in vivo," *Gene Therapy*, 2009, pp. 1-11.
Michele A. Kutzler et al., "DNA vaccines: ready for prime time?," *Nat Rev Gen*, 2008, 9:776-788.
Dominick J. Laddy et al., "Immunogenicity of novel consensus-based DNA vaccines against avian influenza," *Vaccine*, 2007, 25:2984-2989.
Mathura P. Ramanathan et al., "Coimmunization with an optimized IL15 plasmid adjuvant enhances humoral immunity via stimulating B cells induced by genetically engineered DNA vaccines expressing consensus JEV and WNV E DIII," *Vaccine*, 2009, doi:10.1016/j.vaccine.2009.01.137.
Mathura P. Ramanathan et al., "Development of a novel DNA SynCon™ tetravalent dengue vaccine that elicit immune responses against four serotypes," *Vaccine*, 2009, 27:6444-6453.
Maja Rupnik et al., "*Clostridium difficile* infection: new developments in epidemiology and pathogenesis," *Nat Rev Microb*, 2009, 7:526-536.
Chiara Sandolo et al., "Encapsulation of Cwp84 into pectin beads for oral vaccination against *Clostridium difficile*," *European Journal of Pharmaceutics and Biopharmaceutics*, 2011, 79:566-573.
An. et al., "Determination of Glycosylation Sites and Site-specific Heterogeneity in Glycoproteins", *Curr. Opin. Chem. Biol.*, vol. 13(4):421-426 (Oct. 2009).

* cited by examiner

B

TcdA RBD

SLFYFDPIEFNLVTGWQTINGKKYYFDINTGAALTSYKIINGKHFYFNNDGVMQLGVFKGPDGFEYF
APANTQNNNIEGQAIVYQSKFLTLNGKKYYFDNNSKAVTGWRIINNEKYYFNPNNAIAAVGLQVIDN
NKYYFNPDTAIISKGWQTVNGSRYYFDTDTAIAFNGYKTIDGKHFYFDSDCVVKIGVFSTSNGFEYF
APANTYNNNIEGQAIVYQSKFLTLNGKKYYFDNNSKAVTGWQTIDSKKYYFNTNTAEAATGWQTID
GKKYYFNTNTAEAATGWQTIDGKKYYFNTNTAIASTGYTIINGKHFYFNTDGIMQIGVFKGPNGFEY
FAPANTDANNIEGQAILYQNEFLTLNGKKYYFGSDSKAVTGWRIINNKKYYFNPNNAIAAIHLCTINN
DKYYFSYDGILQNGYITIERNNFYFDANNESKMVTGVFKGPNGFEYFAPANTHNNNIEGQAIVYQN
KFLTLNGKKYYFDNDSKAVTGWQTIDGKKYYFNLNTAEAATGWQTIDGKKYYFNLNTAEAATGWQ
TIDGKKYYFNTNTFIASTGYTSINGKHFYFNTDGIMQIGVFKGPNGFEYFAPANTDANNIEGQAILYQ
NKFLTLNGKKYYFGSDSKAVTGLRTIDGKKYYFNTNTAVAVTGWQTINGKKYYFNTNTSIASTGYTII
SGKHFYFNTDGIMQIGVFKGPDGFEYFAPANTDANNIEGQAIRYQNRFLYLHDNIYYFGNNSKAAT
GWVTIDGNRYYFEPNTAMGANGYKTIDNKNFYFRNGLPQIGVFKGSNGFEYFAPANTDANNIEGQ
AIRYQNRFLHLLGKIYYFGNNSKAVTGWQTINGKVYYFMPDTAMAAAGGLFEIDGVIYFFGVDGVK
APGIYG (SEQ ID NO:1)

TcdB RBD

SLYYFKPPVNNLITGFVTVGDDKYYFNPINGGAASIGETIIDDKNYYFNQSGVLQTGVFSTEDGFK
YFAPANTLDENLEGEAIDFTGKLIIDENIYYFDDNYRGAVEWKELDGEMHYFSPETGKAFKGLNQI
GDYKYYFNSDGVMQKGFVSINDNKHYFDDSGVMKVGYTEIDGKHFYFAENGEMQIGVFNTEDG
FKYFAHHNEDLGNEEGEEISYSGILNFNNKIYYFDDSFTAVVGWKDLEDGSKYYFDEDTAEAYIGL
SLINDGQYYFNDDGIMQVGFVTINDKVFYFSDSGIIESGVQNIDDNYFYIDDNGIVQIGVFDTSDGY
KYFAPANTVNDNIYGQAVEYSGLVRVGEDVYYFGETYTIETGWIYDMENESDKYYFNPETKKACK
GINLIDDIKYYFDEKGIMRTGLISFENNNYYFNENGEMQFGYINIEDKMFYFGEDGVMQIGVFNTP
DGFKYFAHQNTLDENFEGESINYTGWLDLDEKRYYFTDEYIAATGSVIIDGEEYYFDPDTAQLVIS
E (SEQ ID NO:2)

TcdA RBD (N→Q)

SLFYFDPIEFNLVTGWQTINGKKYYFDINTGAALTSYKIINGKHFYFNNDGVMQLGVFKGPDGFEYF
APANTQNNNIEGQAIVYQSKFLTLNGKKYYFDQNSKAVTGWRIINNEKYYFNPNNAIAAVGLQVIDN
NKYYFNPDTAIISKGWQTVQGSRYYFDTDTAIAFNGYKTIDGKHFYFDSDCVVKIGVFSTSNGFEYF
APANTYNNNIEGQAIVYQSKFLTLNGKKYYFDQNSKAVTGWQTIDSKKYYFNTNTAEAATGWQTID
GKKYYFNTNTAEAATGWQTIDGKKYYFNTNTAIASTGYTIINGKHFYFNTDGIMQIGVFKGPNGFEY
FAPANTDANNIEGQAILYQNEFLTLNGKKYYFGSDSKAVTGWRIINNKKYYFNPNNAIAAIHLCTINN
DKYYFSYDGILQNGYITIERNNFYFDANQESKMVTGVFKGPNGFEYFAPANTHNNNIEGQAIVYQN
KFLTLNGKKYYFDQDSKAVTGWQTIDGKKYYFNLNTAEAATGWQTIDGKKYYFNLNTAEAATGWQ
TIDGKKYYFNTNTFIASTGYTSINGKHFYFNTDGIMQIGVFKGPNGFEYFAPANTDANNIEGQAILYQ
NKFLTLNGKKYYFGSDSKAVTGLRTIDGKKYYFNTNTAVAVTGWQTINGKKYYFNTQTSIASTGYTII
SGKHFYFNTDGIMQIGVFKGPDGFEYFAPANTDANNIEGQAIRYQNRFLYLHDNIYYFGQNSKAAT
GWVTIDGNRYYFEPNTAMGANGYKTIDNKNFYFRNGLPQIGVFKGSNGFEYFAPANTDANNIEGQ
AIRYQNRFLHLLGKIYYFGQNSKAVTGWQTINGKVYYFMPDTAMAAAGGLFEIDGVIYFFGVDGVK
APGIYG (SEQ ID NO:3)

TcdB RBD (N→Q)

SLYYFKPPVNNLITGFVTVGDDKYYFNPINGGAASIGETIIDDKNYYFQQSGVLQTGVFSTEDGFK
YFAPANTLDENLEGEAIDFTGKLIIDENIYYFDDNYRGAVEWKELDGEMHYFSPETGKAFKGLNQI
GDYKYYFNSDGVMQKGFVSINDNKHYFDDSGVMKVGYTEIDGKHFYFAENGEMQIGVFNTEDG
FKYFAHHNEDLGNEEGEEISYSGILNFNNKIYYFDDSFTAVVGWKDLEDGSKYYFDEDTAEAYIGL
SLINDGQYYFNDDGIMQVGFVTINDKVFYFSDSGIIESGVQNIDDNYFYIDDNGIVQIGVFDTSDGY
KYFAPANTVNDNIYGQAVEYSGLVRVGEDVYYFGETYTIETGWIYDMEQESDKYYFNPETKKAC
KGINLIDDIKYYFDEKGIMRTGLISFENNNYYFNENGEMQFGYINIEDKMFYFGEDGVMQIGVFNT
PDGFKYFAHQNTLDENFEGESIQYTGWLDLDEKRYYFTDEYIAATGSVIIDGEEYYFDPDTAQLVI
SE (SEQ ID NO:4)

B

TcdA neutralization

(bar chart: % cell rounding vs Media, 1:10, 1:100, 1:1000, 1:10000 for TcdA RBD N→Q, and 1:10 for pVAX)

TcdB Neutralization

(bar chart: % cell rounding vs Media, 1:10, 1:100, 1:1000, 1:10000 for TcdB RBD N→Q, and 1:10 for pVAX)

SEQUENCE LISTING

```
<160> NUMBER OF SEQ ID NOS: 4

<210> SEQ ID NO 1
<211> LENGTH: 872
<212> TYPE: PRT
<213> ORGANISM: Clostridium difficile

<400> SEQUENCE: 1

Ser Leu Phe Tyr Phe Asp Pro Ile Glu Phe Asn Leu Val Thr Gly Trp
1               5                   10                  15

Gln Thr Ile Asn Gly Lys Lys Tyr Tyr Phe Asp Ile Asn Thr Gly Ala
            20                  25                  30

Ala Leu Thr Ser Tyr Lys Ile Ile Asn Gly Lys His Phe Tyr Phe Asn
        35                  40                  45

Asn Asp Gly Val Met Gln Leu Gly Val Phe Lys Gly Pro Asp Gly Phe
    50                  55                  60

Glu Tyr Phe Ala Pro Ala Asn Thr Gln Asn Asn Asn Ile Glu Gly Gln
65                  70                  75                  80

Ala Ile Val Tyr Gln Ser Lys Phe Leu Thr Leu Asn Gly Lys Lys Tyr
                85                  90                  95
```

```
Tyr Phe Asp Asn Asn Ser Lys Ala Val Thr Gly Trp Arg Ile Ile Asn
            100                 105                 110

Asn Glu Lys Tyr Tyr Phe Asn Pro Asn Asn Ala Ile Ala Ala Val Gly
        115                 120                 125

Leu Gln Val Ile Asp Asn Asn Lys Tyr Tyr Phe Asn Pro Asp Thr Ala
    130                 135                 140

Ile Ile Ser Lys Gly Trp Gln Thr Val Asn Gly Ser Arg Tyr Tyr Phe
145                 150                 155                 160

Asp Thr Asp Thr Ala Ile Ala Phe Asn Gly Tyr Lys Thr Ile Asp Gly
                165                 170                 175

Lys His Phe Tyr Phe Asp Ser Asp Cys Val Val Lys Ile Gly Val Phe
            180                 185                 190

Ser Thr Ser Asn Gly Phe Glu Tyr Phe Ala Pro Ala Asn Thr Tyr Asn
        195                 200                 205

Asn Asn Ile Glu Gly Gln Ala Ile Val Tyr Gln Ser Lys Phe Leu Thr
    210                 215                 220

Leu Asn Gly Lys Lys Tyr Tyr Phe Asp Asn Asn Ser Lys Ala Val Thr
225                 230                 235                 240

Gly Trp Gln Thr Ile Asp Ser Lys Lys Tyr Tyr Phe Asn Thr Asn Thr
                245                 250                 255

Ala Glu Ala Ala Thr Gly Trp Gln Thr Ile Asp Gly Lys Lys Tyr Tyr
            260                 265                 270

Phe Asn Thr Asn Thr Ala Glu Ala Ala Thr Gly Trp Gln Thr Ile Asp
        275                 280                 285

Gly Lys Lys Tyr Tyr Phe Asn Thr Asn Thr Ala Ile Ala Ser Thr Gly
    290                 295                 300

Tyr Thr Ile Ile Asn Gly Lys His Phe Tyr Phe Asn Thr Asp Gly Ile
305                 310                 315                 320

Met Gln Ile Gly Val Phe Lys Gly Pro Asn Gly Phe Glu Tyr Phe Ala
                325                 330                 335

Pro Ala Asn Thr Asp Ala Asn Asn Ile Glu Gly Gln Ala Ile Leu Tyr
            340                 345                 350

Gln Asn Glu Phe Leu Thr Leu Asn Gly Lys Lys Tyr Tyr Phe Gly Ser
        355                 360                 365

Asp Ser Lys Ala Val Thr Gly Trp Arg Ile Ile Asn Asn Lys Lys Tyr
    370                 375                 380

Tyr Phe Asn Pro Asn Asn Ala Ile Ala Ala Ile His Leu Cys Thr Ile
385                 390                 395                 400

Asn Asn Asp Lys Tyr Tyr Phe Ser Tyr Asp Gly Ile Leu Gln Asn Gly
                405                 410                 415

Tyr Ile Thr Ile Glu Arg Asn Asn Phe Tyr Phe Asp Ala Asn Asn Glu
            420                 425                 430

Ser Lys Met Val Thr Gly Val Phe Lys Gly Pro Asn Gly Phe Glu Tyr
        435                 440                 445

Phe Ala Pro Ala Asn Thr His Asn Asn Asn Ile Glu Gly Gln Ala Ile
    450                 455                 460

Val Tyr Gln Asn Lys Phe Leu Thr Leu Asn Gly Lys Lys Tyr Tyr Phe
465                 470                 475                 480

Asp Asn Asp Ser Lys Ala Val Thr Gly Trp Gln Thr Ile Asp Gly Lys
                485                 490                 495
```

```
Lys Tyr Tyr Phe Asn Leu Asn Thr Ala Glu Ala Ala Thr Gly Trp Gln
            500                 505                 510

Thr Ile Asp Gly Lys Lys Tyr Tyr Phe Asn Leu Asn Thr Ala Glu Ala
        515                 520                 525

Ala Thr Gly Trp Gln Thr Ile Asp Gly Lys Lys Tyr Tyr Phe Asn Thr
    530                 535                 540

Asn Thr Phe Ile Ala Ser Thr Gly Tyr Thr Ser Ile Asn Gly Lys His
545                 550                 555                 560

Phe Tyr Phe Asn Thr Asp Gly Ile Met Gln Ile Gly Val Phe Lys Gly
                565                 570                 575

Pro Asn Gly Phe Glu Tyr Phe Ala Pro Ala Asn Thr Asp Ala Asn Asn
            580                 585                 590

Ile Glu Gly Gln Ala Ile Leu Tyr Gln Asn Lys Phe Leu Thr Leu Asn
            595                 600                 605

Gly Lys Lys Tyr Tyr Phe Gly Ser Asp Ser Lys Ala Val Thr Gly Leu
            610                 615                 620

Arg Thr Ile Asp Gly Lys Lys Tyr Tyr Phe Asn Thr Asn Thr Ala Val
625                 630                 635                 640

Ala Val Thr Gly Trp Gln Thr Ile Asn Gly Lys Lys Tyr Tyr Phe Asn
                645                 650                 655

Thr Asn Thr Ser Ile Ala Ser Thr Gly Tyr Thr Ile Ile Ser Gly Lys
                660                 665                 670

His Phe Tyr Phe Asn Thr Asp Gly Ile Met Gln Ile Gly Val Phe Lys
                675                 680                 685

Gly Pro Asp Gly Phe Glu Tyr Phe Ala Pro Ala Asn Thr Asp Ala Asn
            690                 695                 700

Asn Ile Glu Gly Gln Ala Ile Arg Tyr Gln Asn Arg Phe Leu Tyr Leu
705                 710                 715                 720

His Asp Asn Ile Tyr Tyr Phe Gly Asn Asn Ser Lys Ala Ala Thr Gly
                725                 730                 735

Trp Val Thr Ile Asp Gly Asn Arg Tyr Tyr Phe Glu Pro Asn Thr Ala
                740                 745                 750

Met Gly Ala Asn Gly Tyr Lys Thr Ile Asp Asn Lys Asn Phe Tyr Phe
            755                 760                 765

Arg Asn Gly Leu Pro Gln Ile Gly Val Phe Lys Gly Ser Asn Gly Phe
770                 775                 780

Glu Tyr Phe Ala Pro Ala Asn Thr Asp Ala Asn Asn Ile Glu Gly Gln
785                 790                 795                 800

Ala Ile Arg Tyr Gln Asn Arg Phe Leu His Leu Leu Gly Lys Ile Tyr
                805                 810                 815

Tyr Phe Gly Asn Asn Ser Lys Ala Val Thr Gly Trp Gln Thr Ile Asn
                820                 825                 830

Gly Lys Val Tyr Tyr Phe Met Pro Asp Thr Ala Met Ala Ala Ala Gly
            835                 840                 845

Gly Leu Phe Glu Ile Asp Gly Val Ile Tyr Phe Phe Gly Val Asp Gly
            850                 855                 860

Val Lys Ala Pro Gly Ile Tyr Gly
865                 870

<210> SEQ ID NO 2
<211> LENGTH: 526
<212> TYPE: PRT
<213> ORGANISM: Clostridium difficile
```

<400> SEQUENCE: 2

```
Ser Leu Tyr Tyr Phe Lys Pro Pro Val Asn Asn Leu Ile Thr Gly Phe
  1               5                  10                  15

Val Thr Val Gly Asp Asp Lys Tyr Tyr Phe Asn Pro Ile Asn Gly Gly
                 20                  25                  30

Ala Ala Ser Ile Gly Glu Thr Ile Ile Asp Asp Lys Asn Tyr Tyr Phe
             35                  40                  45

Asn Gln Ser Gly Val Leu Gln Thr Gly Val Phe Ser Thr Glu Asp Gly
         50                  55                  60

Phe Lys Tyr Phe Ala Pro Ala Asn Thr Leu Asp Glu Asn Leu Glu Gly
 65                  70                  75                  80

Glu Ala Ile Asp Phe Thr Gly Lys Leu Ile Ile Asp Glu Asn Ile Tyr
                 85                  90                  95

Tyr Phe Asp Asp Asn Tyr Arg Gly Ala Val Glu Trp Lys Glu Leu Asp
                100                 105                 110

Gly Glu Met His Tyr Phe Ser Pro Glu Thr Gly Lys Ala Phe Lys Gly
            115                 120                 125

Leu Asn Gln Ile Gly Asp Tyr Lys Tyr Tyr Phe Asn Ser Asp Gly Val
        130                 135                 140

Met Gln Lys Gly Phe Val Ser Ile Asn Asp Asn Lys His Tyr Phe Asp
145                 150                 155                 160

Asp Ser Gly Val Met Lys Val Gly Tyr Thr Glu Ile Asp Gly Lys His
                165                 170                 175

Phe Tyr Phe Ala Glu Asn Gly Glu Met Gln Ile Gly Val Phe Asn Thr
            180                 185                 190

Glu Asp Gly Phe Lys Tyr Phe Ala His His Asn Glu Asp Leu Gly Asn
        195                 200                 205

Glu Glu Gly Glu Glu Ile Ser Tyr Ser Gly Ile Leu Asn Phe Asn Asn
    210                 215                 220

Lys Ile Tyr Tyr Phe Asp Asp Ser Phe Thr Ala Val Val Gly Trp Lys
225                 230                 235                 240

Asp Leu Glu Asp Gly Ser Lys Tyr Tyr Phe Asp Glu Asp Thr Ala Glu
                245                 250                 255

Ala Tyr Ile Gly Leu Ser Leu Ile Asn Asp Gly Gln Tyr Tyr Phe Asn
            260                 265                 270

Asp Asp Gly Ile Met Gln Val Gly Phe Val Thr Ile Asn Asp Lys Val
        275                 280                 285

Phe Tyr Phe Ser Asp Ser Gly Ile Ile Glu Ser Gly Val Gln Asn Ile
    290                 295                 300

Asp Asp Asn Tyr Phe Tyr Ile Asp Asp Asn Gly Ile Val Gln Ile Gly
305                 310                 315                 320

Val Phe Asp Thr Ser Asp Gly Tyr Lys Tyr Phe Ala Pro Ala Asn Thr
                325                 330                 335

Val Asn Asp Asn Ile Tyr Gly Gln Ala Val Glu Tyr Ser Gly Leu Val
            340                 345                 350

Arg Val Gly Glu Asp Val Tyr Tyr Phe Gly Glu Thr Tyr Thr Ile Glu
        355                 360                 365

Thr Gly Trp Ile Tyr Asp Met Glu Asn Glu Ser Asp Lys Tyr Tyr Phe
370                 375                 380

Asn Pro Glu Thr Lys Lys Ala Cys Lys Gly Ile Asn Leu Ile Asp Asp
                390                 395                 400

Ile Lys Tyr Tyr Phe Asp Glu Lys Gly Ile Met Arg Thr Gly Leu Ile
            405                 410                 415
```

```
Ser Phe Glu Asn Asn Tyr Phe Asn Glu Asn Gly Glu Met Gln
            420                 425                 430

Phe Gly Tyr Ile Asn Ile Glu Asp Lys Met Phe Tyr Phe Gly Glu Asp
        435                 440                 445

Gly Val Met Gln Ile Gly Val Phe Asn Thr Pro Asp Gly Phe Lys Tyr
        450                 455                 460

Phe Ala His Gln Asn Thr Leu Asp Glu Asn Phe Glu Gly Glu Ser Ile
465                 470                 475                 480

Asn Tyr Thr Gly Trp Leu Asp Leu Asp Glu Lys Arg Tyr Tyr Phe Thr
                485                 490                 495

Asp Glu Tyr Ile Ala Ala Thr Gly Ser Val Ile Ile Asp Gly Glu Glu
            500                 505                 510

Tyr Tyr Phe Asp Pro Asp Thr Ala Gln Leu Val Ile Ser Glu
            515                 520                 525

<210> SEQ ID NO 3
<211> LENGTH: 872
<212> TYPE: PRT
<213> ORGANISM: Clostridium difficile

<400> SEQUENCE: 3

Ser Leu Phe Tyr Phe Asp Pro Ile Glu Phe Asn Leu Val Thr Gly Trp
1               5                   10                  15

Gln Thr Ile Asn Gly Lys Lys Tyr Tyr Phe Asp Ile Asn Thr Gly Ala
            20                  25                  30

Ala Leu Thr Ser Tyr Lys Ile Ile Asn Gly Lys His Phe Tyr Phe Asn
        35                  40                  45

Asn Asp Gly Val Met Gln Leu Gly Val Phe Lys Gly Pro Asp Gly Phe
    50                  55                  60

Glu Tyr Phe Ala Pro Ala Asn Thr Gln Asn Asn Asn Ile Glu Gly Gln
65                  70                  75                  80

Ala Ile Val Tyr Gln Ser Lys Phe Leu Thr Leu Asn Gly Lys Lys Tyr
                85                  90                  95

Tyr Phe Asp Gln Asn Ser Lys Ala Val Thr Gly Trp Arg Ile Ile Asn
            100                 105                 110

Asn Glu Lys Tyr Tyr Phe Asn Pro Asn Asn Ala Ile Ala Ala Val Gly
        115                 120                 125

Leu Gln Val Ile Asp Asn Asn Lys Tyr Tyr Phe Asn Pro Asp Thr Ala
    130                 135                 140

Ile Ile Ser Lys Gly Trp Gln Thr Val Gln Gly Ser Arg Tyr Tyr Phe
145                 150                 155                 160

Asp Thr Asp Thr Ala Ile Ala Phe Asn Gly Tyr Lys Thr Ile Asp Gly
                165                 170                 175

Lys His Phe Tyr Phe Asp Ser Asp Cys Val Val Lys Ile Gly Val Phe
            180                 185                 190

Ser Thr Ser Asn Gly Phe Glu Tyr Phe Ala Pro Ala Asn Thr Tyr Asn
        195                 200                 205

Asn Asn Ile Glu Gly Gln Ala Ile Val Tyr Gln Ser Lys Phe Leu Thr
    210                 215                 220

Leu Asn Gly Lys Lys Tyr Tyr Phe Asp Gln Asn Ser Lys Ala Val Thr
225                 230                 235                 240

Gly Trp Gln Thr Ile Asp Ser Lys Lys Tyr Tyr Phe Asn Thr Asn Thr
                245                 250                 255

Ala Glu Ala Ala Thr Gly Trp Gln Thr Ile Asp Gly Lys Lys Tyr Tyr
            260                 265                 270
```

```
Phe Asn Thr Asn Thr Ala Glu Ala Thr Gly Trp Gln Thr Ile Asp
            275                 280                 285
Gly Lys Lys Tyr Tyr Phe Asn Thr Asn Thr Ala Ile Ala Ser Thr Gly
290                 295                 300
Tyr Thr Ile Ile Asn Gly Lys His Phe Tyr Phe Asn Thr Asp Gly Ile
305                 310                 315                 320
Met Gln Ile Gly Val Phe Lys Gly Pro Asn Gly Phe Glu Tyr Phe Ala
                325                 330                 335
Pro Ala Asn Thr Asp Ala Asn Asn Ile Glu Gly Gln Ala Ile Leu Tyr
                340                 345                 350
Gln Asn Glu Phe Leu Thr Leu Asn Gly Lys Lys Tyr Tyr Phe Gly Ser
            355                 360                 365
Asp Ser Lys Ala Val Thr Gly Trp Arg Ile Ile Asn Asn Lys Lys Tyr
        370                 375                 380
Tyr Phe Asn Pro Asn Asn Ala Ile Ala Ala Ile His Leu Cys Thr Ile
385                 390                 395                 400
Asn Asn Asp Lys Tyr Tyr Phe Ser Tyr Asp Gly Ile Leu Gln Asn Gly
                405                 410                 415
Tyr Ile Thr Ile Glu Arg Asn Asn Phe Tyr Phe Asp Ala Asn Gln Glu
                420                 425                 430
Ser Lys Met Val Thr Gly Val Phe Lys Gly Pro Asn Gly Phe Glu Tyr
            435                 440                 445
Phe Ala Pro Ala Asn Thr His Asn Asn Asn Ile Glu Gly Gln Ala Ile
        450                 455                 460
Val Tyr Gln Asn Lys Phe Leu Thr Leu Asn Gly Lys Lys Tyr Tyr Phe
465                 470                 475                 480
Asp Gln Asp Ser Lys Ala Val Thr Gly Trp Gln Thr Ile Asp Gly Lys
                485                 490                 495
Lys Tyr Tyr Phe Asn Leu Asn Thr Ala Glu Ala Ala Thr Gly Trp Gln
                500                 505                 510
Thr Ile Asp Gly Lys Lys Tyr Tyr Phe Asn Leu Asn Thr Ala Glu Ala
            515                 520                 525
Ala Thr Gly Trp Gln Thr Ile Asp Gly Lys Lys Tyr Tyr Phe Asn Thr
        530                 535                 540
Asn Thr Phe Ile Ala Ser Thr Gly Tyr Thr Ser Ile Asn Gly Lys His
545                 550                 555                 560
Phe Tyr Phe Asn Thr Asp Gly Ile Met Gln Ile Gly Val Phe Lys Gly
                565                 570                 575
Pro Asn Gly Phe Glu Tyr Phe Ala Pro Ala Asn Thr Asp Ala Asn Asn
                580                 585                 590
Ile Glu Gly Gln Ala Ile Leu Tyr Gln Asn Lys Phe Leu Thr Leu Asn
            595                 600                 605
Gly Lys Lys Tyr Tyr Phe Gly Ser Asp Ser Lys Ala Val Thr Gly Leu
        610                 615                 620
Arg Thr Ile Asp Gly Lys Lys Tyr Tyr Phe Asn Thr Asn Thr Ala Val
625                 630                 635                 640
Ala Val Thr Gly Trp Gln Thr Ile Asn Gly Lys Lys Tyr Tyr Phe Asn
                645                 650                 655
Thr Gln Thr Ser Ile Ala Ser Thr Gly Tyr Thr Ile Ile Ser Gly Lys
                660                 665                 670
His Phe Tyr Phe Asn Thr Asp Gly Ile Met Gln Ile Gly Val Phe Lys
            675                 680                 685
```

Gly Pro Asp Gly Phe Glu Tyr Phe Ala Pro Ala Asn Thr Asp Ala Asn
690                 695                 700

Asn Ile Glu Gly Gln Ala Ile Arg Tyr Gln Asn Arg Phe Leu Tyr Leu
705                 710                 715                 720

His Asp Asn Ile Tyr Tyr Phe Gly Gln Asn Ser Lys Ala Ala Thr Gly
            725                 730                 735

Trp Val Thr Ile Asp Gly Asn Arg Tyr Tyr Phe Glu Pro Asn Thr Ala
            740                 745                 750

Met Gly Ala Asn Gly Tyr Lys Thr Ile Asp Asn Lys Asn Phe Tyr Phe
        755                 760                 765

Arg Asn Gly Leu Pro Gln Ile Gly Val Phe Lys Gly Ser Asn Gly Phe
770                 775                 780

Glu Tyr Phe Ala Pro Ala Asn Thr Asp Ala Asn Asn Ile Glu Gly Gln
785                 790                 795                 800

Ala Ile Arg Tyr Gln Asn Arg Phe Leu His Leu Leu Gly Lys Ile Tyr
            805                 810                 815

Tyr Phe Gly Gln Asn Ser Lys Ala Val Thr Gly Trp Gln Thr Ile Asn
            820                 825                 830

Gly Lys Val Tyr Tyr Phe Met Pro Asp Thr Ala Met Ala Ala Ala Gly
        835                 840                 845

Gly Leu Phe Glu Ile Asp Gly Val Ile Tyr Phe Phe Gly Val Asp Gly
850                 855                 860

Val Lys Ala Pro Gly Ile Tyr Gly
865                 870

<210> SEQ ID NO 4
<211> LENGTH: 526
<212> TYPE: PRT
<213> ORGANISM: Clostridium difficile

<400> SEQUENCE: 4

Ser Leu Tyr Tyr Phe Lys Pro Val Asn Asn Leu Ile Thr Gly Phe
1               5                   10                  15

Val Thr Val Gly Asp Asp Lys Tyr Tyr Phe Asn Pro Ile Asn Gly Gly
            20                  25                  30

Ala Ala Ser Ile Gly Glu Thr Ile Ile Asp Asp Lys Asn Tyr Tyr Phe
        35                  40                  45

Gln Gln Ser Gly Val Leu Gln Thr Gly Val Phe Ser Thr Glu Asp Gly
    50                  55                  60

Phe Lys Tyr Phe Ala Pro Ala Asn Thr Leu Asp Glu Asn Leu Glu Gly
65                  70                  75                  80

Glu Ala Ile Asp Phe Thr Gly Lys Leu Ile Ile Asp Glu Asn Ile Tyr
            85                  90                  95

Tyr Phe Asp Asp Asn Tyr Arg Gly Ala Val Glu Trp Lys Glu Leu Asp
            100                 105                 110

Gly Glu Met His Tyr Phe Ser Pro Glu Thr Gly Lys Ala Phe Lys Gly
        115                 120                 125

Leu Asn Gln Ile Gly Asp Tyr Lys Tyr Tyr Phe Asn Ser Asp Gly Val
    130                 135                 140

Met Gln Lys Gly Phe Val Ser Ile Asn Asp Asn Lys His Tyr Phe Asp
145                 150                 155                 160

Asp Ser Gly Val Met Lys Val Gly Tyr Thr Glu Ile Asp Gly Lys His
            165                 170                 175

Phe Tyr Phe Ala Glu Asn Gly Glu Met Gln Ile Gly Val Phe Asn Thr
            180                 185                 190

-continued

```
Glu Asp Gly Phe Lys Tyr Phe Ala His His Asn Glu Asp Leu Gly Asn
        195                 200                 205

Glu Glu Gly Glu Ile Ser Tyr Ser Gly Ile Leu Asn Phe Asn Asn
    210                 215                 220

Lys Ile Tyr Tyr Phe Asp Asp Ser Phe Thr Ala Val Val Gly Trp Lys
225                 230                 235                 240

Asp Leu Glu Asp Gly Ser Lys Tyr Tyr Phe Asp Glu Asp Thr Ala Glu
            245                 250                 255

Ala Tyr Ile Gly Leu Ser Leu Ile Asn Asp Gly Gln Tyr Tyr Phe Asn
            260                 265                 270

Asp Asp Gly Ile Met Gln Val Gly Phe Val Thr Ile Asn Asp Lys Val
            275                 280                 285

Phe Tyr Phe Ser Asp Ser Gly Ile Ile Glu Ser Gly Val Gln Asn Ile
        290                 295                 300

Asp Asp Asn Tyr Phe Tyr Ile Asp Asp Asn Gly Ile Val Gln Ile Gly
305                 310                 315                 320

Val Phe Asp Thr Ser Asp Gly Tyr Lys Tyr Phe Ala Pro Ala Asn Thr
            325                 330                 335

Val Asn Asp Asn Ile Tyr Gly Gln Ala Val Glu Tyr Ser Gly Leu Val
            340                 345                 350

Arg Val Gly Glu Asp Val Tyr Tyr Phe Gly Glu Thr Tyr Thr Ile Glu
        355                 360                 365

Thr Gly Trp Ile Tyr Asp Met Glu Gln Glu Ser Asp Lys Tyr Tyr Phe
    370                 375                 380

Asn Pro Glu Thr Lys Lys Ala Cys Lys Gly Ile Asn Leu Ile Asp Asp
385                 390                 395                 400

Ile Lys Tyr Tyr Phe Asp Glu Lys Gly Ile Met Arg Thr Gly Leu Ile
            405                 410                 415

Ser Phe Glu Asn Asn Tyr Tyr Phe Asn Glu Asn Gly Glu Met Gln
            420                 425                 430

Phe Gly Tyr Ile Asn Ile Glu Asp Lys Met Phe Tyr Phe Gly Glu Asp
        435                 440                 445

Gly Val Met Gln Ile Gly Val Phe Asn Thr Pro Asp Gly Phe Lys Tyr
450                 455                 460

Phe Ala His Gln Asn Thr Leu Asp Glu Asn Phe Glu Gly Glu Ser Ile
465                 470                 475                 480

Gln Tyr Thr Gly Trp Leu Asp Leu Asp Glu Lys Arg Tyr Tyr Phe Thr
            485                 490                 495

Asp Glu Tyr Ile Ala Ala Thr Gly Ser Val Ile Ile Asp Gly Glu Glu
            500                 505                 510

Tyr Tyr Phe Asp Pro Asp Thr Ala Gln Leu Val Ile Ser Glu
        515                 520                 525
```

CLOSTRIDIUM DIFFICILE DNA VACCINE

CROSS-REFERENCE TO RELATED APPLICATIONS

This application is the U.S. national phase application filed under 35 U.S.C. §371 claiming benefit to International Patent Application No. PCT/US2012/046422, filed on Jul. 12, 2012, which is entitled to priority under 35 U.S.C. §119(e) to U.S. Provisional Patent application Ser. No. 61/506,973, filed Jul. 12, 2011, each of which application is hereby incorporated herein by reference in its entirety.

STATEMENT REGARDING FEDERALLY SPONSORED RESEARCH OR DEVELOPMENT

This invention was made with government support under Contract No. W81XWH-09-1-0382 awarded by the United States Department of Defense. The government has certain rights in the invention.

BACKGROUND OF THE INVENTION

Clostridium difficile (C. difficile) associated disease (CDAD) is a major source of morbidity and mortality, costing the United States healthcare system approximately $1.1 billion/year due to medication costs or surgery leading to prolonged hospital stays. In addition, hospitals are experiencing increased rates of this disease, with physicians documenting markedly increased relapse rates following treatment with metronidazole. Mortality rates due to C. difficile are increasing, and new strains produce higher levels of toxin that are resistant to antibiotics. Colonic infection with C. difficile can result in a spectrum of conditions that range from mild diarrhea to severe colitis with potentially life-threatening complications. Although elderly hospitalized patients receiving antibiotics are still the main group at risk of CDAC, an increase in CDAD in younger populations with no previous contact either with the hospital environment or with antibiotics is emerging. Furthermore, CDAD in specific populations that were previously at low risk, such as children and pregnant women, is increasing. Therefore, protecting those who are most at risk, including those exposed to peri-operative and or prolonged antibiotic use should be a priority and is of the utmost significance.

The gram-positive, anaerobic, spore-forming bacterium C. difficile is recognized as the major cause of hospital-acquired diarrhea (2008, Wilcox et al., J Antimicrob Chemother 62(2): 388-396; 2008, Gould et al., Crit Care 12(1): 203). While as many as 3% of healthy outpatient adults may be colonized with the organism, this rate increases dramatically following hospitalization. Since 2000, extensive publications have described resurgence in the rates and severity of C. difficile disease in North America and Europe (Gould et al., Crit Care 12(1): 203). These events have renewed interest in novel approaches to disease treatment and prevention, including toxin-specific vaccines. Disease results from the production of the major cytotoxins, Toxins A and B, whose clinical manifestations range from asymptomatic carriage to diarrhea, toxic megacolon, and death. Toxins A and B are 300 kD and 270 kD proteins, respectively, and are members of the large clostridial cytotoxin family which share homology with the hemorrhagic and lethal toxins of C. sordelli and the alpha toxin of C. novyi. These glucosyl transferases inactivate a variety of host proteins, including Rho, Rac, and Cdc42, ultimately leading to the ascribed pathologic and clinical changes.

Toxin A is considered to be the principal mediator of C. difficile associated disease in animal models. This Toxin mediates epithelial disruption leading to cellular entry of Toxin B, also an enterotoxin. The Toxins stimulate IL-8 and MIP-2 secretion, and promote neutrophil recruitment (2005, Voth et al., Clin Microbiol Rev 18(2) 247-263). In addition, Toxin B strains (TcdA-TcdB+) have been shown to be more potent that Toxin A strains (TcdA+TcdB-) in causing mucosal necrosis and decreasing barrier function (2009, Rupnik et al., Nat Rev Microbiol 7(7) 526-536). These toxin-mediated events have renewed interest in novel approaches to disease treatment and prevention, including toxin-specific vaccines.

Recent studies highlight the influence of toxin-specific, host antibody responses on the outcome of C. difficile colonization and infection. It has been observed that patients with anti-Toxin A antibodies before colonization with C. difficile spores have been observed as having significantly lower risk of progression to active and severe disease. Once infected, patients who develop strong anti-Toxin antibody responses clear their disease with antimicrobial treatment and remain disease free. Over the past 10 years, several passive and active immunization strategies have been tested against C. difficile infection in animals. These studies have highlighted the importance of the carboxy-terminal receptor-binding domain (RBD) as containing key epitopes for neutralizing the activity of toxin A and toxin B. Finally, intravenous administration of IgG developed against the RBD is protective in mice and hamsters. The role of anti-toxin humoral immune responses in protection against C. difficile disease is further validated by numerous passive and active immunization studies followed by toxin challenge (2010, Leav et al., Vaccine 28(4): 965-969). Further, it has been shown that transcutaneous immunization with formalin-treated C. difficile toxin A (CDA) induces systemic and mucosal anti-CDA immune responses (2007, Ghose et al., Infect Immun 75(6): 2826-2832). However, clinical indications for immune based therapies against C. difficile have not been fully defined for passive immunization, as efficacy of pooled immunoglobulin preparations is not well established as adjunct therapy (2005, Aslam et al., Lancet Infect Dis 5(9): 549-557). Moreover, there are certain stability issues with toxoid-based vaccine platforms (1995, Torres et al., Infect Immun 62(12): 4619-4627) that may limit their effectiveness in the clinic. Such studies provide strong scientific rationale for development of alternative next generation optimized vaccines against C. difficile Toxins. To that end, promising next generation DNA vaccine technology that includes mucosal targeting adjuvants (2010, Kraynyak et al., Vaccine 28(8):1942-1951; 2010, Kutzler et al., Gene Ther 17(1): 72-82) and electroporation delivery methods has been shown to be effective in the HIV vaccine platform.

DNA-based immunization has a number of advantages that make it an attractive vaccine platform (2006, Hokey et al., Springer Semin Immunopathol 28(3): 267-279; 2008, Kutzler and Weiner, Nat Rev Genet 9(10): 776-788). First, it has an improved safety profile compared to live attenuated viruses, which may revert back to their virulent form or spread to unintended individuals. The following qualities of DNA-based vaccines and adjuvants support use of this platform over toxoid-based strategies: ease of manipulation, proven production techniques, stability, and the lack of a cold chain requirement. In addition, DNA vaccines have been shown to elicit humoral and cellular responses and confer protection in small and larger animal models (2008, Kutzler and Weiner, Nat Rev Genet 9(10): 776-788). Taken together, these advantages make DNA-based immunizations a desirable vaccine modality for *C. difficile*. Increasing the transfection efficiency of target cells through various physical delivery methods including Electroporation is an area that has had success in the field. Importantly, the DNA vaccine platform has shown promise and is currently in Phase I clinical trials testing highly optimized antigenic constructs, supporting the safety and potential of this platform (2009, Yin et al., Virology 393(1): 49-55; 2005, Kutzler et al., J Immunol 175(1): 112-123; 2007, Chong et al, Vaccine 25(26): 4967-4982). DNA vaccines have historically been associated with induction of cellular immune responses, although more recently, it has demonstrated that delivery of DNA vaccines using Electroporation can be used to induce robust humoral responses in addition to strong cellular responses. This includes the induction of neutralizing antibody titers in animal models for a number of diseases—including avian influenza (2008, Laddy et al., PLoS One 3(6): e2517; 2007, Laddy et al., Vaccine 25(16): 2984-2989), smallpox (2011, Hirao et al, J Infect Dis 203(1): 95-102), dengue (2009, Ramanathan et al., Vaccine 27(46): 6444-6453; 2009, Ramanathan et al, Vaccine 27(32): 4370-4380), and chikungunya (2011, Mallilankaraman et al., PLoS Negl Trop Dis 5(1): e928).

While numerous platforms have been studied as candidate *C. difficile* vaccines (2007, Ghose et al., Infect Immun 75(6): 2826-2832; 2011, Oberli et al., Chem Biol 18(5): 580-588; 2011, Pechine et al., FEMS Immunol Med Microbiol June 24; 2011, Permpoonpattana et al., Infect Immun 79(6): 2295-2302; 2011, Sandolo et al., Eur J Pharm Biopharm June 1; 2008, Ni Eidhin et al, FEMS Immunol Med Microbiol 52(2): 207-218; 2008, Taylor et al., Vaccine 26(27-28): 3404-3409; 2009, Gardiner et al., Vaccine 27(27): 3598-3604), the number of products in the clinical pipeline is lacking. Given the tremendous cost and increasing prevalence of *C. difficile* infections, there is thus a need in the art for an effective vaccine therapy which protects against *C. difficile* associated disease. The present invention addresses this unmet need in the art.

SUMMARY

In various embodiments, the invention is a vaccine comprising at least one nucleic acid expressing at least a portion of at least one of *C. difficile* toxin A and *C. difficile* toxin B. In one embodiment, the invention is a vaccine comprising at least one nucleic acid selected from the group consisting of a nucleic acid encoding a polypeptide comprising the amino acid sequence of SEQ ID NO:3 and a nucleic acid encoding a polypeptide comprising the amino acid sequence of SEQ ID NO:4. In another embodiment, the vaccine further comprises a nucleic acid encoding a secretory leader peptide. In a particular embodiment, the secretory leader peptide is an IgE secretory leader peptide. In some embodiments, the nucleic acid is incorporated into one expression vector, while in other embodiments, the nucleic acid is incorporated into two or more expression vectors. In some embodiments, the at least one nucleic acid is codon-optimized for expression in a human cell.

In another embodiment, the invention is a method of immunizing a mammal against *C. difficile* comprising the step of administering at least one vaccine of the invention to a tissue of the mammal. In some embodiments, the method of immunization comprising administering the vaccine to the tissue of the mammal and electroporating cells of the tissue of the mammal with a current effective to permit entry of the nucleic acid molecules into the cells. In some embodiments, the tissue of the mammal is muscle. In other embodiments, the tissue of the mammal is skin. In some embodiments, the vaccine is administered by intramuscular or intradermal injection. In one embodiment, the mammal is not currently infected with *C. difficile* and the vaccine induces a protective immune response. In some embodiments, the protective immune response includes at least one antibody that specifically binds to at least one polypeptide of the group consisting of the polypeptide of SEQ ID NO:3 and the polypeptide of SEQ ID NO:4. In some embodiments, the mammal is human.

In another embodiment, the invention is a method of immunizing a mammal infected with *C. difficile* comprising the step of administering at least one vaccine of the invention to a tissue of the mammal. In some embodiments, the method of immunization comprising administering the vaccine to the tissue of the mammal and electroporating cells of the tissue of the mammal with a current effective to permit entry of the nucleic acid molecules into the cells. In some embodiments, the tissue of the mammal is muscle. In other embodiments, the tissue of the mammal is skin. In some embodiments, the vaccine is administered by intramuscular or intradermal injection. In one embodiment, the mammal is currently infected with *C. difficile* and the vaccine induces a therapeutic immune response. In some embodiments, the therapeutic immune response includes at least one antibody that specifically binds to at least one polypeptide of the group consisting of the polypeptide of SEQ ID NO:3 and the polypeptide of SEQ ID NO:4. In some embodiments, the mammal is a human.

In a one embodiment, the invention is an isolated polypeptide comprising the amino acid sequence of SEQ ID NO:3. In another embodiment, the invention is a nucleic acid encoding the amino acid sequence of SEQ ID NO:3. In one embodiment, the invention is an isolated polypeptide comprising the amino acid sequence of SEQ ID NO:4. In another embodiment, the invention is an isolated nucleic acid encoding the amino acid sequence of SEQ ID NO:4. In a further embodiment, the invention is a composition comprising an isolated polypeptide comprising the amino acid sequence of SEQ ID NO:3 and an isolated polypeptide comprising the amino acid sequence of SEQ ID NO:4. In a still further embodiment, the invention is a composition comprising an isolated nucleic acid encoding the amino acid sequence of SEQ ID NO:3 and an isolated nucleic acid encoding the amino acid sequence of SEQ ID NO:4.

BRIEF DESCRIPTION OF THE DRAWINGS

The following detailed description of preferred embodiments of the invention will be better understood when read in conjunction with the appended drawings. For the purpose of illustrating the invention, there are shown in the drawings embodiments which are presently preferred. It should be understood, however, that the invention is not limited to the precise arrangements and instrumentalities of the embodiments shown in the drawings.

FIG. 1, comprising FIGS. 1A and 1B, depicts sequences of the RBD of Toxin A and the RBD of Toxin B, as well as experiments demonstrating the in vitro expression of the toxin RBDs.

FIG. 6 depicts the results of experiments demonstrating that sera from pRBD N→Q immunized animals prevents cell rounding of cells exposed to Toxin A or Toxin B.

FIG. 9, comprising FIGS. 9A-9E, depicts exemplary expression vector construct design and the results of experiments assessing construct expression. (A) Antigen DNA modifications are summarized in the table, left panel. A schematic displaying key components of pVAX (backbone) is shown, right panel. Four plasmids, encoding A or B RBD wt and A or B RBD N→Q were optimized and constructed. (B) Putative N-linked glycosylation sites in the RBD of toxins A and B are underlined. At these sites, Gln was substituted for the first Asn during construction of the DNA vaccine plasmids. (C) Sequences of the RBD of toxins A and B having the first Asn of each putative N-linked glycosylation site substituted with Gln. (D) 293T cells ($3.0 \times 10^5$ cells) were transfected with 2 μg of pRBD N→Q constructs using Lipofectamine 2000. Forty-eight hours post-transfection, lysates (RIPA buffer) and supernatants were harvested, fractionated on SDS-PAGE (4-12%), and transferred to PVDF membrane. Immunodetection was performed with specific mouse antiserum and the expressed proteins were visualized with horseradish peroxidase-conjugated goat anti-mouse IgG using an ECL detection system. (E) Aliquots of lysates and supernatants were digested with 500 U of polypeptide N-glycosidase F (PNGaseF) for 1 hour at 37° C. and deactivated at 65° C. for 15 minutes. Samples were subjected to SDS-PAGE (8%) and immuno detection.

FIG. 11, comprising

FIG. 12, comprising FIGS. 12A-12B, depicts the results of experiments demonstrating that sera from animals immunized with pRBD N→Q can neutralize C. difficile toxin activity in vitro. (A) Vero cells ($5.0 \times 10^4$ cells) were grown to a monolayer (24 hours) in a 96-well plate. Mouse sera was diluted in growth media and added to an equivalent volume of growth media containing enough purified toxin A or toxin B to induce 100% cell rounding. This was mixed gently, incubated for 1 hour at 37° C. and added in duplicate to the 96-well plate. After 20-24 hours, cell rounding was assessed under 10× magnification. Pictures represent the average effect across two wells. Goat anti-Toxin A (List Biologicals) was used as a positive control. (B) Cell rounding was measured by analyzing six random fields per well and averaging the percentage of rounded cells. Results were graphed in comparison to pVAX sera and goat anti-Toxin A.

Figure 16:
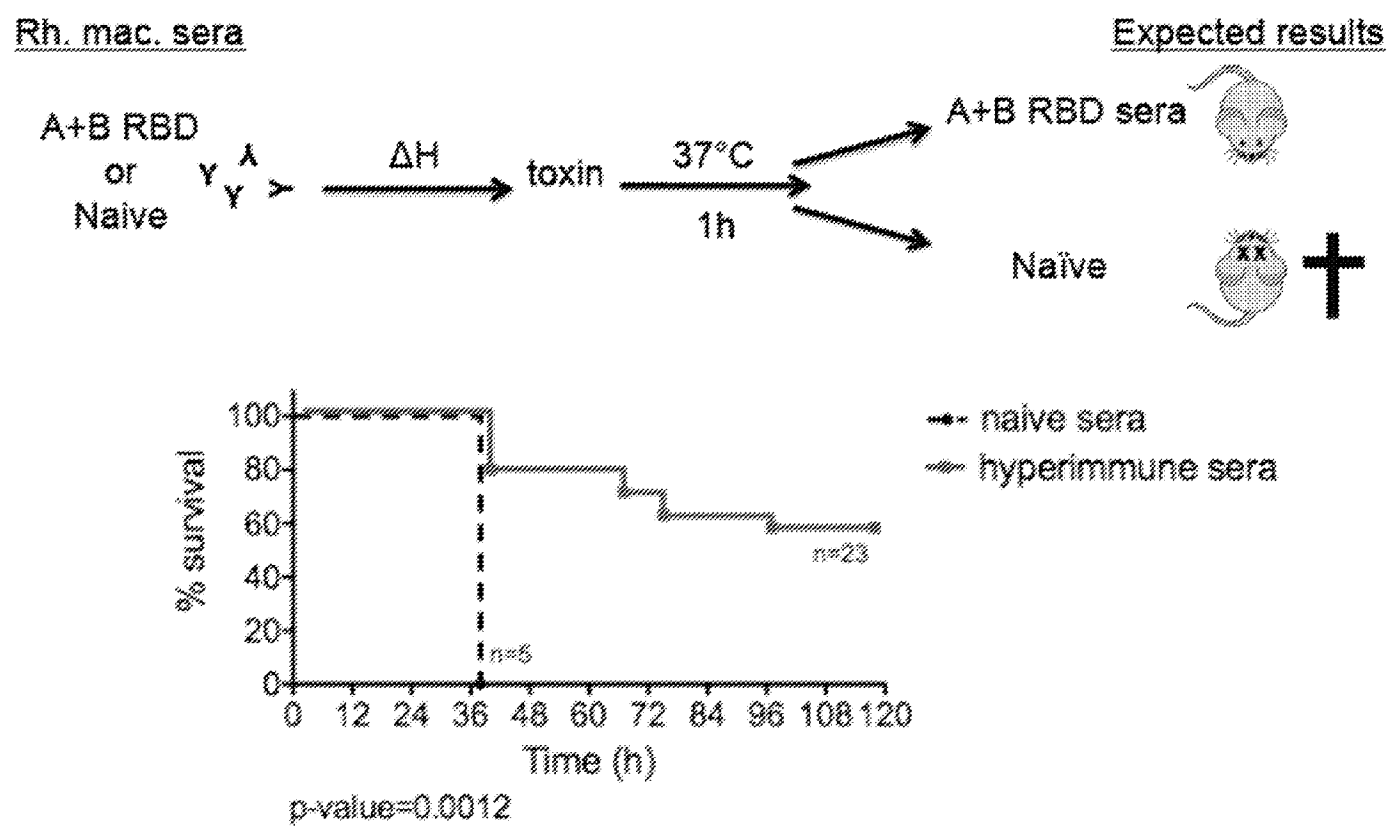

FIG. 16 depicts the results of experiments demonstrating that macaque hyperimmune sera neutralizes the lethal effects of C. difficile toxin in mice.

DETAILED DESCRIPTION

Figure 1A:
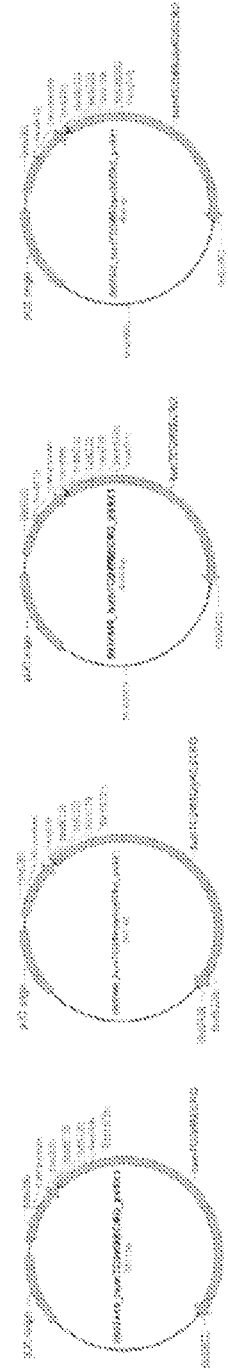

The present invention provides compositions and methods to prevent, inhibit, and treat C. difficile associated disease (CDAD). In one embodiment, the composition of the invention is a vaccine that induces the production of antibodies specific for C. difficile proteins (e.g., toxin A (TcdA) and toxin B (TcdB)). In one embodiment, the composition comprises the receptor binding domain (RBD) of toxin A. In another embodiment, the composition comprises the RBD of toxin B. In another embodiment, the composition comprises the RBD of toxin A and the RBD of toxin B.

In one embodiment, the composition of the invention is a DNA vaccine. In one embodiment, the composition of the invention comprises a nucleic acid sequence encoding the RBD of toxin A. In another embodiment, the composition of the invention comprises a nucleic acid sequence encoding the RBD of toxin B. In another embodiment, the composition comprises a nucleic acid sequence encoding the RBD of toxin A and the RBD of toxin B. In one embodiment, the nucleic acid of the composition is optimized for increased translation and secretion of the RBD polypeptides. In one embodiment, the composition comprises one or more polypeptides selected from SEQ ID NO:1 and SEQ ID NO:2, or a modification thereof. In one embodiment, the composition comprises one or more nucleic acid sequences encoding an amino acid sequence selected from SEQ ID NO:1 and SEQ ID NO:2, or a modification thereof.

In one embodiment, the RBD of toxin A and RBD of toxin B are mutated from wild-type to prevent N-linked glycosylation. Such mutations preserve the glycosylation state of native toxin A and toxin B produced by C. difficile, thereby ensuring effective immunogenicity. In one embodiment, the composition comprises one or more polypeptides selected from SEQ ID NO:3 and SEQ ID NO:4. In one embodiment, the composition comprises one or more nucleic acid sequences encoding an amino acid sequence selected from SEQ ID NO:3 and SEQ ID NO:4.

The invention also provides methods of inducing an immune response for preventing and treating to CDAD. In one embodiment, the methods comprise administering the RBD of toxin A and/or the RBD of toxin B to a subject. In another embodiment, the methods comprise administering a nucleic acid encoding the RBD of toxin A and/or the RBD of toxin B to a subject. In one embodiment the method comprises administering the composition intramuscularly. In one embodiment, the method comprises in vivo electroporation.

Definitions

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described.

As used herein, each of the following terms has the meaning associated with it in this section. It is also to be understood that the terminology used herein is for the purpose of describing particular embodiments only, and is not intended to be limiting.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20% or ±10%, more preferably ±5%, even more preferably ±1%, and still more preferably ±0.1% from the specified value, as such variations are appropriate to perform the disclosed methods.

The term "antibody," as used herein, refers to an immunoglobulin molecule which specifically binds with an antigen. Antibodies can be intact immunoglobulins derived from natural sources or from recombinant sources and can be immunoreactive portions of intact immunoglobulins. The antibodies in the present invention may exist in a variety of forms including, for example, polyclonal antibodies, monoclonal antibodies, Fv, Fab and $F(ab)_2$, as well as single chain antibodies and humanized antibodies (Harlow et al., 1999, In: Using Antibodies: A Laboratory Manual, Cold Spring Harbor Laboratory Press, NY; Harlow et al., 1989, In: Antibodies: A Laboratory Manual, Cold Spring Harbor, N.Y.; Houston et al., 1988, Proc. Natl. Acad. Sci. USA 85:5879-5883; Bird et al., 1988, Science 242:423-426).

The term "antigen" or "Ag" as used herein is defined as a molecule that provokes an immune response. This immune response may involve either antibody production, or the activation of specific immunologically-competent cells, or both. The skilled artisan will understand that any macromolecule, including virtually all proteins or peptides, can serve as an antigen. Furthermore, antigens can be derived from recombinant or genomic DNA. A skilled artisan will understand that any DNA, which comprises a nucleotide sequences or a partial nucleotide sequence encoding a protein that elicits an immune response therefore encodes an "antigen" as that term is used herein. Furthermore, one skilled in the art will understand that an antigen need not be encoded solely by a full length nucleotide sequence of a gene. It is readily apparent that the present invention includes, but is not limited to, the use of partial nucleotide sequences of more than one gene and that these nucleotide sequences are arranged in various combinations to elicit the desired immune response. Moreover, a skilled artisan will understand that an antigen need not be encoded by a "gene" at all. It is readily apparent that an antigen can be generated synthesized or can be derived from a biological sample.

As used herein, the term "autologous" is meant to refer to any material derived from the same individual to which it is later to be re-introduced into the individual.

As used herein, by "combination therapy" is meant that a first agent is administered in conjunction with another agent. "In conjunction with" refers to administration of one treatment modality in addition to another treatment modality. As such, "in conjunction with" refers to administration of one treatment modality before, during, or after delivery of the other treatment modality to the individual. Such combinations are considered to be part of a single treatment regimen or regime.

As used herein, the term "concurrent administration" means that the administration of the first therapy and that of a second therapy in a combination therapy overlap with each other.

A "disease" is a state of health of an animal wherein the animal cannot maintain homeostasis, and wherein if the disease is not ameliorated then the animal's health continues to deteriorate. In contrast, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

An "effective amount" as used herein, means an amount which provides a therapeutic or prophylactic benefit.

The term "expression" as used herein is defined as the transcription and/or translation of a particular nucleotide sequence driven by its promoter.

"Expression vector" refers to a vector comprising a recombinant polynucleotide comprising expression control sequences operatively linked to a nucleotide sequence to be expressed. An expression vector comprises sufficient cis-acting elements for expression; other elements for expression can be supplied by the host cell or in an in vitro expression system. Expression vectors include all those known in the art, such as cosmids, plasmids (e.g., naked or contained in liposomes) and viruses (e.g., lentiviruses, retroviruses, adenoviruses, and adeno-associated viruses) that incorporate the recombinant polynucleotide.

"Homologous" refers to the sequence similarity or sequence identity between two polypeptides or between two nucleic acid molecules. When a position in both of the two compared sequences is occupied by the same base or amino acid monomer subunit, e.g., if a position in each of two DNA molecules is occupied by adenine, then the molecules are homologous at that position. The percent of homology between two sequences is a function of the number of matching or homologous positions shared by the two sequences divided by the number of positions compared×100. For example, if 6 of 10 of the positions in two sequences are matched or homologous then the two sequences are 60% homologous. By way of example, the DNA sequences ATTGCC and TATGGC share 50% homology. Generally, a comparison is made when two sequences are aligned to give maximum homology.

The term "immunoglobulin" or "Ig," as used herein, is defined as a class of proteins, which function as antibodies. Antibodies expressed by B cells are sometimes referred to as the BCR (B cell receptor) or antigen receptor. The five members included in this class of proteins are IgA, IgG, IgM, IgD, and IgE. IgA is the primary antibody that is present in body secretions, such as saliva, tears, breast milk, gastrointestinal secretions and mucus secretions of the respiratory and genitourinary tracts. IgG is the most common circulating antibody. IgM is the main immunoglobulin produced in the primary immune response in most subjects. It is the most efficient immunoglobulin in agglutination, complement fixation, and other antibody responses, and is important in defense against bacteria and viruses. IgD is the immunoglobulin that has no known antibody function, but may serve as an antigen receptor. IgE is the immunoglobulin that mediates immediate hypersensitivity by causing release of mediators from mast cells and basophils upon exposure to allergen.

As used herein, the term "immune response" includes T-cell mediated and/or B-cell mediated immune responses. Exemplary immune responses include T cell responses, e.g., cytokine production and cellular cytotoxicity, and B cell responses, e.g., antibody production. In addition, the term immune response includes immune responses that are indirectly affected by T cell activation, e.g., antibody production (humoral responses) and activation of cytokine responsive cells, e.g., macrophages. Immune cells involved in the immune response include lymphocytes, such as B cells and T cells (CD4+, CD8+, Th1 and Th2 cells); antigen presenting cells (e.g., professional antigen presenting cells such as dendritic cells, macrophages, B lymphocytes, Langerhans cells, and non-professional antigen presenting cells such as keratinocytes, endothelial cells, astrocytes, fibroblasts, oligodendrocytes); natural killer cells; myeloid cells, such as macrophages, eosinophils, mast cells, basophils, and granulocytes.

"Isolated" means altered or removed from the natural state. For example, a nucleic acid or a peptide naturally present in a living animal is not "isolated," but the same nucleic acid or peptide partially or completely separated from the coexisting materials of its natural state is "isolated." An isolated nucleic acid or protein can exist in substantially purified form, or can exist in a non-native environment such as, for example, a host cell.

"Parenteral" administration of an immunogenic composition includes, e.g., subcutaneous (s.c.), intravenous (i.v.), intramuscular (i.m.), or intrasternal injection, or infusion techniques.

The terms "patient," "subject," "individual," and the like are used interchangeably herein, and refer to any animal, or cells thereof whether in vitro or in situ, amenable to the methods described herein. In certain non-limiting embodiments, the patient, subject or individual is a human.

The term "simultaneous administration," as used herein, means that a first therapy and second therapy in a combination therapy are administered with a time separation of no more than about 15 minutes, such as no more than about any of 10, 5, or 1 minutes. When the first and second therapies are administered simultaneously, the first and second therapies may be contained in the same composition (e.g., a composition comprising both a first and second therapy) or in separate compositions (e.g., a first therapy in one composition and a second therapy is contained in another composition).

By the term "specifically binds," as used herein with respect to an antibody, is meant an antibody which recognizes a specific antigen, but does not substantially recognize or bind other molecules in a sample. For example, an antibody that specifically binds to an antigen from one species may also bind to that antigen from one or more species. But, such cross-species reactivity does not itself alter the classification of an antibody as specific. In another example, an antibody that specifically binds to an antigen may also bind to different allelic forms of the antigen. However, such cross reactivity does not itself alter the classification of an antibody as specific. In some instances, the terms "specific binding" or "specifically binding," can be used in reference to the interaction of an antibody, a protein, or a peptide with a second chemical species, to mean that the interaction is dependent upon the presence of a particular structure (e.g., an antigenic determinant or epitope) on the chemical species; for example, an antibody recognizes and binds to a specific protein structure rather than to proteins generally. If an antibody is specific for epitope "A," the presence of a molecule containing epitope A (or free, unlabeled A), in a reaction containing labeled "A" and the antibody, will reduce the amount of labeled A bound to the antibody.

The term "therapeutic" as used herein means a treatment and/or prophylaxis. A therapeutic effect is obtained by suppression, remission, or eradication of a disease state.

The term "therapeutically effective amount" refers to the amount of the subject compound that will elicit the biological or medical response of a tissue, system, or subject that is being sought by the researcher, veterinarian, medical doctor or other clinician. The term "therapeutically effective amount" includes that amount of a compound that, when administered, is sufficient to prevent development of, or alleviate to some extent, one or more of the signs or symptoms of the disorder or disease being treated. The therapeutically effective amount will vary depending on the compound, the disease and its severity and the age, weight, etc., of the subject to be treated.

To "treat" a disease as the term is used herein, means to reduce the frequency or severity of at least one sign or symptom of a disease or disorder experienced by a subject.

The term "transfected" or "transformed" or "transduced" as used herein refers to a process by which exogenous nucleic acid is transferred or introduced into the host cell. A "transfected" or "transformed" or "transduced" cell is one which has been transfected, transformed or transduced with exogenous nucleic acid. The cell includes the primary subject cell and its progeny.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Description

The invention relates to the discovery that the administration of a region of a *Clostridium difficile* (*C. difficile*) toxin A and/or toxin B nucleic acid into a subject results in the production of toxin specific antibodies. Thus, the present invention provides a polypeptide or a combination of polypeptides, a polynucleotide or a combination of polynucleotides, pharmaceutical and vaccine compositions, including some which are useful in modulating of immune responses, and in the inhibition, prevention and treatment of CDAD and related disorders.

The invention provides an immunological composition comprising a polypeptide epitope or combination of polypeptide epitopes derived from *C. difficile* toxin A (TcdA) and *C. difficile* toxin B (TcdB) useful in eliciting an immune response. The composition comprising one or more polypeptides of the invention not only are useful as a prophylactic therapeutic agent for immunoprotection, but is also useful as a therapeutic agent for treatment of an ongoing condition associated with CDAD in a subject.

In one embodiment, the composition comprises the receptor binding domain (RBD) of toxin A. In one embodiment, the composition comprises a mutant receptor binding domain (RBD) of toxin A. In one embodiment, the composition comprises the RBD of toxin B. In another embodiment, the composition comprises a mutant RBD of toxin B. In one embodiment, the composition is a polynucleotide encoding the RBD of toxin A and/or the RBD of toxin B. In another embodiment, the composition is a polynucleotide encoding a mutant RBD of toxin A and/or the RBD of toxin B. The composition may be altered to increase immunogenicity. For example, in one embodiment, the polynucleotide of the composition comprises regions which increase the translation and secretion of the RBD polypeptides. In another embodiment, the nucleotide sequence encoding wild type RBD of toxin A and/or toxin B is mutated to remove potential sites for N-linked glycosylation. That is, in one embodiment, the composition comprises a nucleotide sequence encoding a mutant RBD of toxin A and/or mutant RBD of toxin B.

The present invention also provides methods of preventing, inhibiting, and treating CDAD. In one embodiment, the methods of the invention induce immunity against *C. difficile*, by generating an immune response directed to a *C. difficile* toxin, such as toxin A and/or toxin B. In one embodiment, the methods of the invention induce production of toxin A and/or toxin B-specific antibodies. In one embodiment, the methods of the invention prevent *C. difficile* related pathology. In one embodiment, the methods of the invention comprise administering a composition comprising at least a portion of toxin A (e.g. RBD) and/or at least a portion of toxin B (e.g., RBD), or variants thereof, to a subject. In another embodiment, the methods of the invention comprise administering a composition comprising a nucleic acid sequence encoding the RBD of toxin A and/or the RBD of toxin B, or variants thereof, to a subject. In one embodiment, the methods comprise administering a DNA vaccine to a subject, thereby inducing immunity to *C. difficile*. In one embodiment, the compositions are administered intramuscularly to a subject. In one embodiment, the method comprises in vivo electroporation.

Compositions

The present invention provides compositions, including polypeptides, nucleotides, vectors, and vaccines, that when administered to a mammal, elicit an immune response directed against *C. difficile*, including an immune response directed against toxin A and/or toxin B (e.g., anti-toxin A and anti-toxin B antibodies). Further, when the compositions are administered to a mammal, they elicit an immune response that serves to protect the inoculated mammal against conditions associated with CDAD. As exemplified herein, the composition can be obtained in large quantities for use as a vaccine.

The composition of the invention is also useful as a diagnostic reagent for assessing the presence or absence of an anti-toxin A and/or anti-toxin B immune response in a mammal. Such an assessment is made by obtaining serum or cells from the mammal and contacting it with a polypeptide, or a combination of polypeptides, of the invention in a standard assay known in the art for detecting binding to the polypeptide.

In one embodiment, the present invention provides compositions that are useful as immunomodulatory agents, for example, in stimulating immune responses and in preventing *C. difficile* related pathology.

It is shown herein that the RBD of toxin A and toxin B can be used as immunostimulatory agents to induce the production of toxin A and toxin B specific antibodies and protect against *C. difficile* induced pathology. Therefore, in one embodiment, the composition of the invention comprises the RBD region, or fragment thereof, of the toxin A polypeptide. In another embodiment, the composition of the invention comprises the RBD region, or fragment thereof, of a mutant toxin A polypeptide. In one embodiment, the composition of the invention comprises the RBD region, or fragment thereof, of the toxin B polypeptide. In another embodiment, the composition of the invention comprises the RBD region, or fragment thereof, of a mutant toxin B polypeptide. In one embodiment, the composition of the invention comprises the RBD regions, or fragments thereof, of both toxin A and toxin B. In another embodiment, the composition of the invention comprises the RBD regions, or fragments thereof, of both a mutant toxin A and mutant toxin B.

The present invention also provides polynucleotides that encode the polypeptides described herein. For example, in one embodiment, the composition of the present invention comprises a polynucleotide encoding the RBD, or fragment thereof, of toxin A polypeptide. In another embodiment, the composition of the invention comprises a polynucleotide encoding the RBD region, or fragment thereof, of a mutant toxin A polypeptide. In one embodiment, the composition of the present invention comprises a polynucleotide encoding the RBD, or fragment thereof, of toxin B polypeptide. In another embodiment, the composition of the invention comprises a polynucleotide encoding the RBD region, or fragment thereof, of a mutant toxin B polypeptide. In one embodiment, the composition of the invention comprises the RBD regions, or fragments thereof, of both toxin A and toxin B polypeptides. In another embodiment, the composition of the invention comprises the RBD regions, or fragments thereof, of both mutant toxin A and mutant toxin B polypeptides. The polynucleotide can be RNA or DNA. In one embodiment, the composition comprises a DNA vaccine.

In one embodiment, the composition comprises an RBD that is mutated from wild-type, or alternatively a polynucleotide encoding an RBD that is mutated from wild-type. The present invention is partly based upon the discovery that producing polypeptides with mutations of potential sites of N-linked glycosylation within the RBD region induces the production of toxin-specific antibodies and the prevention of toxin-induced pathology. The mutations preserve the glycosylation state of bacterium-produced toxins, thereby ensuring that antibodies produced against the administered compositions will also recognize bacterium-produced toxin. Translation of wild-type toxin A RBD and toxin B RBD in eukaryotes would result in glycosylated toxin A RBD and toxin B RBD. The immunogenicity against glycosylated toxin A RBD and toxin B RBD may not be effective in recognizing bacterial toxin A and toxin B during *C. difficile* infection, thereby rendering the inoculation less effective or ineffective. In one embodiment, the composition comprises toxin A RBD and/or toxin B RBD containing asparagine to glutamine (N→Q) mutations at one or more native asparagine residues found in the wild type sequences. In one embodiment, the composition comprises a nucleic acid encoding toxin A RBD and/or toxin B RBD containing asparagine to glutamine (N→Q) mutations at one or more native asparagine residues found in the wild type sequences.

In one embodiment, the invention provides a composition comprising a polypeptide comprising an amino acid sequence of SEQ ID NO:1, or a fragment or variant thereof. In another embodiment, the invention provides a composition comprising a polypeptide comprising an amino acid sequence of SEQ ID NO:2, or a fragment or variant thereof. In another embodiment, the composition comprises a polypeptide comprising an amino acid sequence of SEQ ID NO:1 and a polypeptide comprising an amino acid sequence of SEQ ID NO:2, or fragments or variant thereof.

In one embodiment, the invention provides a composition comprising a polypeptide comprising an amino acid sequence of SEQ ID NO:3, or a fragment or variant thereof. In another embodiment, the invention provides a composition comprising a polypeptide comprising an amino acid sequence of SEQ ID NO:4, or a fragment or variant thereof. In another embodiment, the composition comprises a polypeptide comprising an amino acid sequence of SEQ ID NO:3 and a polypeptide comprising an amino acid sequence of SEQ ID NO:4, or fragments or variant thereof.

In one embodiment, the invention provides a polypeptide, or a fragment of a polypeptide, a homolog, a variant, a derivative or a salt of a polypeptide having the sequence of any one or more of SEQ ID NOS:1-4, wherein the immunogenic activity of the polypeptide or fragment thereof is retained.

The invention should also be construed to include any form of a polypeptide having substantial homology to the polypeptides disclosed herein. Preferably, a polypeptide which is "substantially homologous" is about 50% homologous, more preferably about 70% homologous, even more preferably about 80% homologous, more preferably about 90% homologous, even more preferably, about 95% homologous, and even more preferably about 99% homologous to amino acid sequence of the polypeptides disclosed herein.

According to yet another embodiment, the polypeptide or combination of polypeptides of the present invention are capable of generating a toxin A and/or toxin B-specific immune response. In another embodiment, the polypeptide or combination of polypeptides of the present invention are capable of generating toxin A and/or toxin B-specific antibodies.

Furthermore, in another embodiment, the present invention provides a polypeptide useful for preventing, inhibiting, and treating CDAD, wherein the polypeptide is selected from the group consisting of a polypeptide, a fragment of a polypeptide, a homolog, a variant, a derivative or a salt of a polypeptide having the sequence of any one or more of SEQ ID NOS:1-4, wherein the immunogenic activity of the polypeptide or fragment is retained.

Polypeptides of the present invention can be prepared using well known techniques. For example, the polypeptides can be prepared synthetically, using either recombinant DNA technology or chemical synthesis. Polypeptides of the present invention may be synthesized individually or as longer polypeptides composed of two or more polypeptides. The polypeptides of the present invention are preferably isolated, i.e., substantially free of other naturally occurring host cell proteins and fragments thereof.

The polypeptides of the present invention may contain modifications, such as glycosylation, aglycosylation, side chain oxidation, or phosphorylation; so long as the modifications do not destroy the biological activity of the polypeptides. Other modifications include incorporation of D-amino acids or other amino acid mimetics that can be used, for example, to increase the serum half-life of the polypeptides.

The polypeptides of the invention can be modified whereby the amino acid is substituted for a different amino acid in which the properties of the amino acid side-chain are conserved (a process known as conservative amino acid substitution). Examples of properties of amino acid side chains are hydrophobic amino acids (A, I, L, M, F, P, W, Y, V), hydrophilic amino acids (R, D, N, C, E, Q, G, H, K, S, T), and side chains having the following functional groups or characteristics in common: an aliphatic side-chain (G, A, V, L, I, P); a hydroxyl group containing side-chain (S, T, Y); a sulfur atom containing side-chain (C, M); a carboxylic acid and amide containing side-chain (D, N, E, Q); a base containing side-chain (R, K, H); and an aromatic containing side-chain (H, F, Y, W). Note that the parenthetic letters indicate the one-letter codes of amino acids.

The polypeptides of the invention can be prepared as a combination, which includes two or more of polypeptides of the invention, for use as a vaccine for prevention or treatment of CDAD. The polypeptides may be in a cocktail or may be conjugated to each other using standard techniques. For example, the polypeptides can be expressed as a single polypeptide sequence. The polypeptides in the combination may be the same or different.

The present invention should also be construed to encompass "mutants," "derivatives," and "variants" of the polypeptides of the invention (or of the DNA encoding the same) which mutants, derivatives and variants are polypeptides which are altered in one or more amino acids (or, when referring to the nucleotide sequence encoding the same, are altered in one or more base pairs) such that the resulting polypeptide (or DNA) is not identical to the sequences recited herein, but has the same biological property as the polypeptides disclosed herein.

The invention also provides a polynucleotide encoding at least one polypeptide selected from a polypeptide having the sequence of any one or more of SEQ ID NOS:1-4. In one embodiment, the invention provides a composition comprising a nucleic acid sequence encoding the amino acid sequence of any one or more of SEQ ID NOS:1-4.

The nucleic acid sequences include both the DNA sequence that is transcribed into RNA and the RNA sequence that is translated into a polypeptide. According to other embodiments, the polynucleotides of the invention are inferred from the amino acid sequence of the polypeptides of the invention. As is known in the art several alternative polynucleotides are possible due to redundant codons, while retaining the biological activity of the translated polypeptides.

Further, the invention encompasses an isolated nucleic acid encoding a polypeptide having substantial homology to the polypeptides disclosed herein. Preferably, the nucleotide sequence of an isolated nucleic acid encoding a polypeptide of the invention is "substantially homologous," that is, is about 60% homologous, more preferably about 70% homologous, even more preferably about 80% homologous, more preferably about 90% homologous, even more preferably, about 95% homologous, and even more preferably about 99% homologous to a nucleotide sequence of an isolated nucleic acid encoding a polypeptide of the invention.

It is to be understood explicitly that the scope of the present invention encompasses homologs, analogs, variants, fragments, derivatives and salts, including shorter and longer polypeptides and polynucleotides, as well as polypeptide and polynucleotide analogs with one or more amino acid or nucleic acid substitution, as well as amino acid or nucleic acid derivatives, non-natural amino or nucleic acids and synthetic amino or nucleic acids as are known in the art, with the stipulation that these modifications must preserve the immunologic activity of the original molecule. Specifically any active fragments of the active polypeptides as well as extensions, conjugates and mixtures are included and are disclosed herein according to the principles of the present invention.

The invention should be construed to include any and all isolated nucleic acids which are homologous to the nucleic acids described and referenced herein, provided these homologous nucleic acids encode polypeptides having the biological activity of the polypeptides disclosed herein.

The skilled artisan would understand that the nucleic acids of the invention encompass an RNA or a DNA sequence encoding a polypeptide of the invention, and any modified forms thereof, including chemical modifications of the DNA or RNA which render the nucleotide sequence more stable when it is cell free or when it is associated with a cell. Chemical modifications of nucleotides may also be used to enhance the efficiency with which a nucleotide sequence is taken up by a cell or the efficiency with which it is expressed in a cell. Any and all combinations of modifications of the nucleotide sequences are contemplated in the present invention.

Further, any number of procedures may be used for the generation of mutant, derivative or variant forms of a protein of the invention using recombinant DNA methodology well known in the art such as, for example, that described in Sambrook and Russell, supra, and Ausubel et al., supra. Procedures for the introduction of amino acid changes in a polypeptide or polypeptide by altering the DNA sequence encoding the polypeptide are well known in the art and are also described in these, and other, treatises.

Vectors

The nucleic acids encoding the polypeptide or combinations of polypeptides of the invention of the invention can be incorporated into suitable vectors, including but not limited to, plasmids and retroviral vectors. Such vectors are well known in the art and are therefore not described in detail herein.

In one embodiment, the invention includes a nucleic acid sequence encoding one or more polypeptides of the invention operably linked to a nucleic acid comprising a promoter/regulatory sequence such that the nucleic acid is preferably capable of directing expression of the protein encoded by the nucleic acid. Thus, the invention encompasses expression vectors and methods for the introduction of exogenous DNA into cells with concomitant expression of the exogenous DNA in the cells such as those described, for example, in Sambrook et al. (2001, Molecular Cloning: A Laboratory Manual, Cold Spring Harbor Laboratory, New York), and in Ausubel et al. (1997, Current Protocols in Molecular Biology, John Wiley & Sons, New York). The incorporation of a desired polynucleotide into a vector and the choice of vectors is well-known in the art as described in, for example, Sambrook et al., supra, and Ausubel et al., supra.

The polynucleotide can be cloned into a number of types of vectors. However, the present invention should not be construed to be limited to any particular vector. Instead, the present invention should be construed to encompass a wide plethora of vectors which are readily available and/or well-known in the art. For example, the polynucleotide of the invention can be cloned into a vector including, but not limited to a plasmid, a phagemid, a phage derivative, an animal virus, and a cosmid. Vectors of particular interest include expression vectors, replication vectors, probe generation vectors, and sequencing vectors.

In specific embodiments, the expression vector is selected from the group consisting of a viral vector, a bacterial vector and a mammalian cell vector. Numerous expression vector systems exist that comprise at least a part or all of the compositions discussed above. Prokaryote- and/or eukaryote-vector based systems can be employed for use with the present invention to produce polynucleotides, or their cognate polypeptides. Many such systems are commercially and widely available.

Further, the expression vector may be provided to a cell in the form of a viral vector. Viral vector technology is well known in the art and is described, for example, in Sambrook et al. (2001), and in Ausubel et al. (1997), and in other virology and molecular biology manuals. Viruses, which are useful as vectors include, but are not limited to, retroviruses, adenoviruses, adeno-associated viruses, herpes viruses, and lentiviruses. In general, a suitable vector contains an origin of replication functional in at least one organism, a promoter sequence, convenient restriction endonuclease sites, and one or more selectable markers. (See, e.g., WO 01/96584; WO 01/29058; and U.S. Pat. No. 6,326,193.

For expression of the desired nucleotide sequences of the invention, at least one module in each promoter functions to position the start site for RNA synthesis. The best known example of this is the TATA box, but in some promoters lacking a TATA box, such as the promoter for the mammalian terminal deoxynucleotidyl transferase gene and the promoter for the SV40 genes, a discrete element overlying the start site itself helps to fix the place of initiation.

Additional promoter elements, i.e., enhancers, regulate the frequency of transcriptional initiation. Typically, these are located in the region 30-110 bp upstream of the start site, although a number of promoters have recently been shown to contain functional elements downstream of the start site as well. The spacing between promoter elements frequently is flexible, so that promoter function is preserved when elements are inverted or moved relative to one another. In the thymidine kinase (tk) promoter, the spacing between promoter elements can be increased to 50 bp apart before activity begins to decline. Depending on the promoter, it appears that individual elements can function either cooperatively or independently to activate transcription.

A promoter may be one naturally associated with a gene or polynucleotide sequence, as may be obtained by isolating the 5' non-coding sequences located upstream of the coding segment and/or exon. Such a promoter can be referred to as "endogenous." Similarly, an enhancer may be one naturally associated with a polynucleotide sequence, located either downstream or upstream of that sequence. Alternatively, certain advantages will be gained by positioning the coding polynucleotide segment under the control of a recombinant or heterologous promoter, which refers to a promoter that is not normally associated with a polynucleotide sequence in its natural environment. A recombinant or heterologous enhancer refers also to an enhancer not normally associated with a polynucleotide sequence in its natural environment. Such promoters or enhancers may include promoters or enhancers of other genes, and promoters or enhancers isolated from any other prokaryotic, viral, or eukaryotic cell, and promoters or enhancers not "naturally occurring," i.e., containing different elements of different transcriptional regulatory regions, and/or mutations that alter expression. In addition to producing nucleic acid sequences of promoters and enhancers synthetically, sequences may be produced using recombinant cloning and/or nucleic acid amplification technology, including PCR, in connection with the compositions disclosed herein (U.S. Pat. Nos. 4,683,202, 5,928,906). Furthermore, it is contemplated the control sequences that direct transcription and/or expression of sequences within non-nuclear organelles such as mitochondria, chloroplasts, and the like, can be employed as well.

Naturally, it will be important to employ a promoter and/or enhancer that effectively directs the expression of the DNA segment in the cell type, organelle, and organism chosen for expression. Those of skill in the art of molecular biology generally know how to use promoters, enhancers, and cell type combinations for protein expression, for example, see Sambrook et al. (2001). The promoters employed may be constitutive, tissue-specific, inducible, and/or useful under the appropriate conditions to direct high level expression of the introduced DNA segment, such as is advantageous in the large-scale production of recombinant proteins and/or polypeptides. The promoter may be heterologous or endogenous.

One example of a constitutive promoter sequence is the immediate early cytomegalovirus (CMV) promoter sequence. This promoter sequence is a strong constitutive promoter sequence capable of driving high levels of expression of any polynucleotide sequence operatively linked thereto. However, other constitutive promoter sequences may also be used, including, but not limited to the simian virus 40 (SV40) early promoter, mouse mammary tumor virus (MMTV), human immunodeficiency virus (HIV) long terminal repeat (LTR) promoter, Moloney virus promoter, the avian leukemia virus promoter, Epstein-Barr virus immediate early promoter, Rous sarcoma virus promoter, as well as human gene promoters such as, but not limited to, the actin promoter, the myosin promoter, the hemoglobin promoter, and the muscle creatine promoter. Further, the invention should not be limited to the use of constitutive promoters. Inducible promoters are also contemplated as part of the invention. The use of an inducible promoter in the invention provides a molecular switch capable of turning on expression of the polynucleotide sequence which it is operatively linked when such expression is desired, or turning off the expression when expression is not desired. Examples of inducible promoters include, but are not limited to a metallothionine promoter, a glucocorticoid promoter, a progesterone promoter, and a tetracycline promoter. Further, the invention includes the use of a tissue-specific promoter, where the promoter is active only in a desired tissue. Tissue-specific promoters are well known in the art and include, but are not limited to, the HER-2 promoter and the PSA associated promoter sequences.

In order to assess the expression of the nucleotide sequences encoding the polypeptide or combinations of polypeptides of the invention, the expression vector to be introduced into a cell can also contain either a selectable marker gene or a reporter gene or both to facilitate identification and selection of expressing cells from the population of cells sought to be transfected or infected through viral vectors. In other embodiments, the selectable marker may be carried on a separate piece of DNA and used in a cotransfection procedure. Both selectable markers and reporter genes may be flanked with appropriate regulatory sequences to enable expression in the host cells. Useful selectable markers are known in the art and include, for example, antibiotic-resistance genes, such as neo and the like.

Reporter genes are used for identifying potentially transfected cells and for evaluating the functionality of regulatory sequences. Reporter genes that encode for easily assayable proteins are well known in the art. In general, a reporter gene is a gene that is not present in or expressed by the recipient organism or tissue and that encodes a protein whose expression is manifested by some easily detectable property, e.g., enzymatic activity. Expression of the reporter gene is assayed at a suitable time after the DNA has been introduced into the recipient cells.

Suitable reporter genes may include genes encoding luciferase, beta-galactosidase, chloramphenicol acetyl transferase, secreted alkaline phosphatase, or the green fluorescent protein gene (see, e.g., Ui-Tei et al., 2000 FEBS Lett. 479:79-82). Suitable expression systems are well known and may be prepared using well known techniques or obtained commercially. Internal deletion constructs may be generated using unique internal restriction sites or by partial digestion of non-unique restriction sites. Constructs may then be transfected into cells that display high levels of siRNA polynucleotide and/or polypeptide expression. In general, the construct with the minimal 5' flanking region showing the highest level of expression of reporter gene is identified as the promoter. Such promoter regions may be linked to a reporter gene and used to evaluate agents for the ability to modulate promoter-driven transcription.

In some embodiments, the expression vector is modified to increase the expression of the desired polypeptide. For example, the vector can undergo codon optimization to improve expression in a given mammal. For example, the vector can be codon-optimized for human expression. In another embodiment, the expression vector comprises an effective secretory leader. An exemplary leader is an IgE leader sequence. In another embodiment, the expression vector comprises a Kozak element to initiate translation. In another embodiment, the nucleic acid is removed of cis-acting sequence motifs/RNA secondary structures that would impede translation. Such modifications, and others, are known in the art for use in DNA vaccines (Kutzler et al, 2008, Nat. Rev. Gen. 9: 776-788; PCT App. No. PCT/US2007/000886; PCT App. No.; PCT/US2004/018962).

Methods of Introducing Nucleic Acid Compositions

The present invention also provides methods of preventing, inhibiting, and treating CDAD in a subject. The methods of the invention provoke an immune response in the subject. In one embodiment, the methods induce the production of toxin A and toxin B specific antibodies. In another embodiment, the methods induce the production of toxin-specific antibody-secreting cells (ASCs). In another embodiment, the methods prevent, reduce or treat CDAD and associated pathologies.

In one embodiment, the methods of the invention comprise administering to a subject, an effective amount of a nucleic acid encoding toxin A RBD and/or toxin B RBD, or variants thereof. In one embodiment, the nucleic acid is delivered to a cell or population of cells. In one embodiment, the nucleic acid is delivered to the cells in vivo, for example, intramuscularly. In another embodiment, the nucleic acid is delivered to the cells ex vivo, where the cells are then administered to the subject. Preferably, the cells also originate from the subject.

In one embodiment, the methods of the invention may be used in an ex vivo vaccination method, where the compositions of the invention are delivered to a cell or cell population, which are administered to the subject, thereby inducing an immune response through, by way of example, the generation of toxin A and/or toxin B antibodies.

In the context of an expression vector, the vector can be readily introduced into a host cell, e.g., mammalian, bacterial, yeast or insect cell by any method in the art. For example, the expression vector can be transferred into a host cell by physical, chemical or biological means.

Physical methods for introducing a polynucleotide into a host cell include calcium phosphate precipitation, lipofection, particle bombardment, microinjection, electroporation, and the like. Methods for producing cells comprising vectors and/or exogenous nucleic acids are well-known in the art. See, for example, Sambrook et al. (2001, Molecular Cloning: A Laboratory Manual, Cold Spring Harbor Laboratory, New York), and in Ausubel et al. (1997, Current Protocols in Molecular Biology, John Wiley & Sons, New York).

Biological methods for introducing a polynucleotide of interest into a host cell include the use of DNA and RNA vectors. Viral vectors, and especially retroviral vectors, have become the most widely used method for inserting genes into mammalian, e.g., human cells. Other viral vectors can be derived from lentivirus, poxviruses, herpes simplex virus I, adenoviruses and adeno-associated viruses, and the like. See, for example, U.S. Pat. Nos. 5,350,674 and 5,585,362.

Chemical means for introducing a polynucleotide into a host cell include colloidal dispersion systems, such as macromolecule complexes, nanocapsules, microspheres, beads, and lipid-based systems including oil-in-water emulsions, micelles, mixed micelles, and liposomes. A preferred colloidal system for use as a delivery vehicle in vitro and in vivo is a liposome (i.e., an artificial membrane vesicle). The preparation and use of such systems is well known in the art.

In the case where a non-viral delivery system is utilized, an exemplary delivery vehicle is a liposome. The use of lipid formulations is contemplated for the introduction of the nucleic acids into a host cell (in vitro, ex vivo or in vivo). In another aspect, the nucleic acid may be associated with a lipid. The nucleic acid associated with a lipid may be encapsulated in the aqueous interior of a liposome, interspersed within the lipid bilayer of a liposome, attached to a liposome via a linking molecule that is associated with both the liposome and the oligonucleotide, entrapped in a liposome, complexed with a liposome, dispersed in a solution containing a lipid, mixed with a lipid, combined with a lipid, contained as a suspension in a lipid, contained or complexed with a micelle, or otherwise associated with a lipid. Lipid, lipid/DNA or lipid/expression vector associated compositions are not limited to any particular structure in solution. For example, they may be present in a bilayer structure, as micelles, or with a "collapsed" structure. They may also simply be interspersed in a solution, possibly forming aggregates that are not uniform in size or shape. Lipids are fatty substances which may be naturally occurring or synthetic lipids. For example, lipids include the fatty droplets that naturally occur in the cytoplasm as well as the class of compounds which contain long-chain aliphatic hydrocarbons and their derivatives, such as fatty acids, alcohols, amines, amino alcohols, and aldehydes.

Lipids suitable for use can be obtained from commercial sources. For example, dimyristyl phosphatidylcholine ("DMPC") can be obtained from Sigma, St. Louis, Mo.; dicetyl phosphate ("DCP") can be obtained from K & K Laboratories (Plainview, N.Y.); cholesterol ("Choi") can be obtained from Calbiochem-Behring; dimyristyl phosphatidylglycerol ("DMPG") and other lipids may be obtained from Avanti Polar Lipids, Inc. (Birmingham, Ala.). Stock solutions of lipids in chloroform or chloroform/methanol can be stored at about −20° C. Chloroform is used as the only solvent since it is more readily evaporated than methanol. "Liposome" is a generic term encompassing a variety of single and multilamellar lipid vehicles formed by the generation of enclosed lipid bilayers or aggregates. Liposomes can be characterized as having vesicular structures with a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh et al., 1991 Glycobiology 5: 505-10). However, compositions that have different structures in solution than the normal vesicular structure are also encompassed. For example, the lipids may assume a micellar structure or merely exist as nonuniform aggregates of lipid molecules. Also contemplated are lipofectamine-nucleic acid complexes.

In other embodiments, the polypeptides of the invention are delivered into cells using in vitro transcribed mRNA. In vitro transcribed mRNA can be delivered into different types of eukaryotic cells as well as into tissues and whole organisms using transfected cells as carriers or cell-free local or systemic delivery of encapsulated, bound or naked mRNA. The method used can be for any purpose where transient expression is required or sufficient.

The methods also provide the ability to control the level of expression over a wide range by changing, for example, the promoter or the amount of input RNA, making it possible to individually regulate the expression level. Furthermore, the PCR-based technique of mRNA production greatly facilitates the design of the chimeric receptor mRNAs with different structures and combination of their domains. For example, varying of different intracellular effector/costimulator domains on multiple chimeric receptors in the same cell allows determination of the structure of the receptor combinations which assess the highest level of cytotoxicity against multi-antigenic targets, and at the same time lowest cytotoxicity toward normal cells.

One advantage of RNA transfection methods of the invention is that RNA transfection is essentially transient and a vector-free: An RNA transgene can be delivered to a cell and expressed therein following a brief in vitro cell activation, as a minimal expressing cassette without the need for any additional viral sequences. Under these conditions, integration of the transgene into the host cell genome is unlikely. Cloning of cells is not necessary because of the efficiency of transfection of the RNA and its ability to uniformly modify the entire lymphocyte population.

Genetic modification of cells with in vitro-transcribed RNA (IVT-RNA) makes use of two different strategies both of which have been successively tested in various animal models. Cells are transfected with in vitro-transcribed RNA by means of lipofection or electroporation. Preferably, it is desirable to stabilize IVT-RNA using various modifications in order to achieve prolonged expression of transferred IVT-RNA.

Some IVT vectors are known in the literature which are utilized in a standardized manner as template for in vitro transcription and which have been genetically modified in such a way that stabilized RNA transcripts are produced. Currently protocols used in the art are based on a plasmid vector with the following structure: a 5' RNA polymerase promoter enabling RNA transcription, followed by a gene of interest which is flanked either 3' and/or 5' by untranslated regions (UTR), and a 3' polyadenyl cassette containing 50-70 A nucleotides. Prior to in vitro transcription, the circular plasmid is linearized downstream of the polyadenyl cassette by type II restriction enzymes (recognition sequence corresponds to cleavage site). The polyadenyl cassette thus corresponds to the later poly(A) sequence in the transcript. As a result of this procedure, some nucleotides remain as part of the enzyme cleavage site after linearization and extend or mask the poly(A) sequence at the 3' end. It is not clear, whether this nonphysiological overhang affects the amount of protein produced intracellularly from such a construct.

RNA has several advantages over more traditional plasmid or viral approaches. Gene expression from an RNA source does not require transcription and the protein product is produced rapidly after the transfection. Further, since the RNA has to only gain access to the cytoplasm, rather than the nucleus, and therefore typical transfection methods result in an extremely high rate of transfection. In addition, plasmid based approaches require that the promoter driving the expression of the gene of interest be active in the cells under study.

In another aspect, the RNA construct can be delivered into the cells by electroporation. See, e.g., the formulations and methodology of electroporation of nucleic acid constructs into mammalian cells as taught in US 2004/0014645, US 2005/0052630A1, US 2005/0070841A1, US 2004/0059285A1, US 2004/0092907A1. The various parameters including electric field strength required for electroporation of any known cell type are generally known in the relevant research literature as well as numerous patents and applications in the field. See e.g., U.S. Pat. Nos. 6,678,556, 7,171,264, and 7,173,116. Apparatus for therapeutic application of electroporation are available commercially, e.g., the MedPulser™ DNA Electroporation Therapy System (Inovio/Genetronics, San Diego, Calif.), and are described in patents such as U.S. Pat. Nos. 6,567,694; 6,516,223, 5,993,434, 6,181,964, 6,241,701, and 6,233,482; electroporation may also be used for transfection of cells in vitro as described e.g. in US20070128708A1. Electroporation may also be utilized to deliver nucleic acids into cells in vitro. Accordingly, electroporation-mediated administration into cells of nucleic acids including expression constructs utilizing any of the many available devices and electroporation systems known to those of skill in the art presents a means for delivering an RNA of interest to a target cell.

Regardless of the method used to introduce exogenous nucleic acids into a host cell or otherwise expose a cell to the inhibitor of the present invention, in order to confirm the presence of the recombinant DNA sequence in the host cell, a variety of assays may be performed. Such assays include, for example, "molecular biological" assays well known to those of skill in the art, such as Southern and Northern blotting, RT-PCR and PCR; "biochemical" assays, such as detecting the presence or absence of a particular polypeptide, e.g., by immunological means (ELISAs and Western blots) or by assays described herein to identify agents falling within the scope of the invention.

Vaccine

For an antigenic composition to be useful as a vaccine, the antigenic composition must induce an immune response to the antigen in a cell, tissue or mammal (e.g., a human). Preferably, the vaccine induces a protective immune response in the mammal. As used herein, an "immunological composition" may comprise, by way of examples, an antigen (e.g., a polypeptide), a nucleic acid encoding an antigen (e.g., an antigen expression vector), or a cell expressing or presenting an antigen or cellular component. In particular embodiments the antigenic composition comprises or encodes all or part of any polypeptide antigen described herein, or an immunologically functional equivalent thereof. In other embodiments, the antigenic composition is in a mixture that comprises an additional immunostimulatory agent or nucleic acids encoding such an agent. Immunostimulatory agents include but are not limited to an additional antigen, an immunomodulator, an antigen presenting cell or an adjuvant. In other embodiments, one or more of the additional agent(s) is covalently bonded to the antigen or an immunostimulatory agent, in any combination. In certain embodiments, the antigenic composition is conjugated to or comprises an HLA anchor motif amino acids.

In the context of the present invention, the term "vaccine" (also referred to as an immunogenic composition) refers to a substance that induces anti-*C. difficile* immunity or suppresses *C. difficile* upon inoculation into an animal.

A vaccine of the present invention may vary in its composition of nucleic acid and/or cellular components. In a non-limiting example, a nucleic encoding an antigen might also be formulated with an adjuvant. Of course, it will be understood that various compositions described herein may further comprise additional components. For example, one or more vaccine components may be comprised in a lipid or liposome. In another non-limiting example, a vaccine may comprise one or more adjuvants. A vaccine of the present invention, and its various components, may be prepared and/or administered by any method disclosed herein or as would be known to one of ordinary skill in the art, in light of the present disclosure.

In one embodiment, the polypeptide vaccine of the invention includes, but is not limited to a polypeptide mixed with adjuvant substances and a polypeptide which is introduced together with an antigen presenting cell (APC). The most common cells used for the latter type of vaccine are bone marrow and peripheral blood derived dendritic cells, as these cells express costimulatory molecules that help activation of T cells. WO00/06723 discloses a cellular vaccine composition which includes an APC presenting tumor associated antigen polypeptides. Presenting the polypeptide can be effected by loading the APC with a polynucleotide (e.g., DNA, RNA) encoding the polypeptide or loading the APC with the polypeptide itself.

Thus, the present invention also encompasses a method of inducing anti-toxin immunity using one or more of polypeptides having the amino acid sequence of SEQ ID NOS: 1-4, or variants thereof. When a certain polypeptide or combination of polypeptides induces an anti-toxin immune response upon inoculation into an animal, the polypeptide or combination of polypeptides are determined to have anti-toxin immunity inducing effect. The induction of the anti-toxin immunity by a polypeptide or combination of polypeptides can be detected by observing in vivo or in vitro the response of the immune system in the host against the polypeptide.

For example, a method for detecting the induction of cytotoxic T lymphocytes is well known. A foreign substance that enters the living body is presented to T cells and B cells by the action of APCs. T cells that respond to the antigen presented by APC in an antigen-specific manner differentiate into cytotoxic T cells (also referred to as cytotoxic T lymphocytes or CTLs) due to stimulation by the antigen. These antigen stimulated cells then proliferate. This process is referred to herein as "activation" of T cells. Therefore, CTL induction by a certain polypeptide or combination of polypeptides of the invention can be evaluated by presenting the polypeptide to a T cell by APC, and detecting the induction of CTL. Furthermore, APCs have the effect of activating CD4+ T cells, CD8+ T cells, macrophages, eosinophils and NK cells.

A method for evaluating the inducing action of CTL using dendritic cells (DCs) as APC is well known in the art. DC is a representative APC having the strongest CTL inducing action among APCs. In this method, the polypeptide or combination of polypeptides are initially contacted with DC and then this DC is contacted with T cells. Detection of T cells having cytotoxic effects against the cells of interest after the contact with DC shows that the polypeptide or combination of polypeptides have an activity of inducing the cytotoxic T cells. Furthermore, the induced immune response can be also examined by measuring IFN-gamma produced and released by CTL in the presence of antigen-presenting cells that carry immobilized polypeptide or combination of polypeptides by visualizing using anti-IFN-gamma antibodies, such as an ELISPOT assay.

Apart from DC, peripheral blood mononuclear cells (PBMCs) may also be used as the APC. The induction of CTL is reported to be enhanced by culturing PBMC in the presence of GM-CSF and IL-4. Similarly, CTL has been shown to be induced by culturing PBMC in the presence of keyhole limpet hemocyanin (KLH) and IL-7.

The polypeptide or combination of polypeptides confirmed to possess CTL inducing activity by these methods are polypeptides having DC activation effect and subsequent CTL inducing activity. Therefore, a polypeptide or combination of polypeptides that induce CTL against toxin A and toxin B are useful as vaccines against *C. difficile* associated disorders. Furthermore, CTL that have acquired cytotoxicity due to presentation of the polypeptide or combination of polypeptides by APC can be also used as vaccines against *C. difficile* associated disorders.

Generally, when using a polypeptide for cellular immunotherapy, efficiency of the CTL-induction can be increased by combining a plurality of polypeptides having different structures and contacting them with DC. Therefore, when stimulating DC with protein fragments, it is advantageous to use a mixture of multiple types of fragments.

The induction of anti-toxin immunity by a polypeptide or combination of polypeptides can be further confirmed by observing the induction of antibody production against the specific toxins. For example, when antibodies against a polypeptide or combination of polypeptides are induced in a laboratory animal immunized with the polypeptide or combination of polypeptides, and when *C. difficile* associated pathology is suppressed by those antibodies, the polypeptide or combination of polypeptides are determined to induce anti-*C. difficile* toxin immunity.

Anti-toxin immunity can be induced by administering a vaccine of the invention, and the induction of anti-toxin immunity enables treatment and prevention of a disease associated with the presence of toxin A and toxin B. Therapy against or prevention of the onset of a disease associated with *C. difficile* may include inhibition of toxin induced actin destabilization, prevention of epithelial disruption, inhibition of toxin-mediated mucosal necrosis, and prevention of decreased barrier function. Decrease in mortality of individuals having a disease associated with *C. difficile*, decrease of the disease markers in the blood, alleviation of detectable symptoms accompanying the disease and such are also included in the therapy or prevention of the disease. Such therapeutic and preventive effects are preferably statistically significant, for example, observed at a significance level of 5% or less, wherein the therapeutic or preventive effect of a vaccine against a disease associated with *C. difficile*, is compared to a control without vaccine administration. For example, Student's t-test, the Mann-Whitney U-test or ANOVA may be used for determining statistical significance.

The invention provides a method for treating, or preventing a disease or condition associated *C. difficile*. The therapeutic compounds or compositions of the invention may be administered prophylactically or therapeutically to subjects suffering from, or at risk of, or susceptible to, developing the disease or condition. Such subjects may be identified using standard clinical methods. In the context of the present invention, prophylactic administration occurs prior to the manifestation of overt clinical symptoms of disease, such that a disease or disorder is prevented or alternatively delayed in its progression. In the context of the field of medicine, the term "prevent" encompasses any activity which reduces the burden of mortality or morbidity from disease. Prevention can occur at primary, secondary and tertiary prevention levels. While primary prevention avoids the development of a disease, secondary and tertiary levels of prevention encompass activities aimed at preventing the progression of a disease and the emergence of symptoms as well as reducing the negative impact of an already established disease by restoring function and reducing disease-related complications.

The polypeptide or combination of polypeptides of the invention having immunological activity, or a polynucleotide or vector encoding such a polypeptide or combination of polypeptides, may be combined with an adjuvant. An adjuvant refers to a compound that enhances the immune response against the polypeptide or combination of polypeptides when administered together (or successively) with the polypeptide having immunological activity. Examples of suitable adjuvants include cholera toxin, salmonella toxin, alum and such, but are not limited thereto. Furthermore, a vaccine of this invention may be combined appropriately with a pharmaceutically acceptable carrier. Examples of such carriers are sterilized water, physiological saline, phosphate buffer, culture fluid and such. Furthermore, the vaccine may contain as necessary, stabilizers, suspensions, preservatives, surfactants and such. The vaccine is administered systemically or locally. Vaccine administration may be performed by single administration or boosted by multiple administrations.

Administration

One skilled in the art recognizes that different methods of delivery may be utilized to administer a vector into a cell. Examples include: (1) methods utilizing physical means, such as electroporation (electricity), a gene gun (physical force) or applying large volumes of a liquid (pressure); and (2) methods wherein said vector is complexed to another entity, such as a liposome, aggregated protein or transporter molecule.

In one embodiment, the methods of the present invention comprise administering a composition comprising a polynucleotide encoding the polypeptides of the invention directly to a subject. Administration of the composition can comprise, for example, intramuscular, intravenous, peritoneal, subcutaneous, intradermal, as well as topical administration. In one embodiment, delivery of the composition is aided by in vivo electroporation. In one embodiment, delivery of the composition comprises a combination of intramuscular administration and in vivo electroporation.

Furthermore, the actual dose and schedule can vary depending on whether the compositions are administered in combination with other pharmaceutical compositions, or depending on inter-individual differences in pharmacokinetics, drug disposition, and metabolism. Similarly, amounts can vary in in vitro applications depending on the particular cell line utilized (e.g., based on the number of vector receptors present on the cell surface, or the ability of the particular vector employed for gene transfer to replicate in that cell line). Furthermore, the amount of vector to be added per cell will likely vary with the length and stability of the therapeutic gene inserted in the vector, as well as also the nature of the sequence, and is particularly a parameter which needs to be determined empirically, and can be altered due to factors not inherent to the methods of the present invention (for instance, the cost associated with synthesis). One skilled in the art can easily make any necessary adjustments in accordance with the exigencies of the particular situation.

Cells containing the therapeutic agent may also contain a suicide gene i.e., a gene which encodes a product that can be used to destroy the cell. In many gene therapy situations, it is desirable to be able to express a gene for therapeutic purposes in a host, cell but also to have the capacity to destroy the host cell at will. The composition can be linked to a suicide gene, whose expression is not activated in the absence of an activator compound. When death of the cell in which both the agent and the suicide gene have been introduced is desired, the activator compound is administered to the cell thereby activating expression of the suicide gene and killing the cell. Examples of suicide gene/prodrug combinations which may be used are herpes simplex virus-thymidine kinase (HSV-tk) and ganciclovir, acyclovir; oxidoreductase and cycloheximide; cytosine deaminase and 5-fluorocytosine; thymidine kinase thymidilate kinase (Tdk::Tmk) and AZT; and deoxycytidine kinase and cytosine arabinoside.

These methods described herein are by no means all-inclusive, and further methods to suit the specific application will be apparent to the ordinary skilled artisan. Moreover, the effective amount of the compositions can be further approximated through analogy to compounds known to exert the desired effect.

Pharmaceutical Compositions

The present invention envisions treating a disease or condition associated with CDAD in a mammal by the administration of a therapeutic composition of the invention to a mammal in need thereof. Administration of the therapeutic composition in accordance with the present invention may be continuous or intermittent, depending, for example, upon the recipient's physiological condition, whether the purpose of the administration is therapeutic or prophylactic, and other factors known to skilled practitioners. The administration of the compositions of the invention may be essentially continuous over a preselected period of time or may be in a series of spaced doses. Both local and systemic administration is contemplated. The amount administered will vary depending on various factors including, but not limited to, the composition chosen, the particular disease, the weight, the physical condition, and the age of the mammal, and whether prevention or treatment is to be achieved. Such factors can be readily determined by the clinician employing animal models or other test systems which are well known to the art.

One or more suitable unit dosage forms having the compositions of the invention, which, as discussed below, may optionally be formulated for sustained release (for example using microencapsulation, see WO 94/07529, and U.S. Pat. No. 4,962,091 the disclosures of which are incorporated by reference herein), can be administered by a variety of routes including parenteral, including by intravenous and intramuscular routes, as well as by direct injection into the diseased tissue. The formulations may, where appropriate, be conveniently presented in discrete unit dosage forms and may be prepared by any of the methods well known to pharmacy. Such methods may include the step of bringing into association the therapeutic agent with liquid carriers, solid matrices, semi-solid carriers, finely divided solid carriers or combinations thereof, and then, if necessary, introducing or shaping the product into the desired delivery system.

When the compositions of the invention are prepared for administration, they are preferably combined with a pharmaceutically acceptable carrier, diluent or excipient to form a pharmaceutical formulation, or unit dosage form. The total active ingredients in such formulations include from 0.1 to 99.9% by weight of the formulation. A "pharmaceutically acceptable" is a carrier, diluent, excipient, and/or salt that is compatible with the other ingredients of the formulation, and not deleterious to the recipient thereof. The active ingredient for administration may be present as a powder or as granules; as a solution, a suspension or an emulsion.

Pharmaceutical formulations containing the compositions of the invention can be prepared by procedures known in the art using well known and readily available ingredients. The compositions of the invention can also be formulated as solutions appropriate for parenteral administration, for instance by intramuscular, subcutaneous or intravenous routes.

The pharmaceutical formulations of the compositions of the invention can also take the form of an aqueous or anhydrous solution or dispersion, or alternatively the form of an emulsion or suspension.

Thus, the composition may be formulated for parenteral administration (e.g., by injection, for example, bolus injection or continuous infusion) and may be presented in unit dose form in ampules, pre-filled syringes, small volume infusion containers or in multi-dose containers with an added preservative. The active ingredients may take such forms as suspensions, solutions, or emulsions in oily or aqueous vehicles, and may contain formulatory agents such as suspending, stabilizing and/or dispersing agents. Alternatively, the active ingredients may be in powder form, obtained by aseptic isolation of sterile solid or by lyophilization from solution, for constitution with a suitable vehicle, e.g., sterile, pyrogen-free water, before use.

It will be appreciated that the unit content of active ingredient or ingredients contained in an individual aerosol dose of each dosage form need not in itself constitute an effective amount for treating the particular indication or disease since the necessary effective amount can be reached by administration of a plurality of dosage units. Moreover, the effective amount may be achieved using less than the dose in the dosage form, either individually, or in a series of administrations.

The pharmaceutical formulations of the present invention may include, as optional ingredients, pharmaceutically acceptable carriers, diluents, solubilizing or emulsifying agents, and salts of the type that are well-known in the art. Specific non-limiting examples of the carriers and/or diluents that are useful in the pharmaceutical formulations of the present invention include water and physiologically acceptable buffered saline solutions, such as phosphate buffered saline solutions pH 7.0-8.0.

The expression vectors, transduced cells, polynucleotides and polypeptides (active ingredients) of this invention can be formulated and administered to treat a variety of disease states by any means that produces contact of the active ingredient with the agent's site of action in the body of the organism. They can be administered by any conventional means available for use in conjunction with pharmaceuticals, either as individual therapeutic active ingredients or in a combination of therapeutic active ingredients. They can be administered alone, but are generally administered with a pharmaceutical carrier selected on the basis of the chosen route of administration and standard pharmaceutical practice.

In general, water, suitable oil, saline, aqueous dextrose (glucose), and related sugar solutions and glycols such as propylene glycol or polyethylene glycols are suitable carriers for parenteral solutions. Solutions for parenteral administration contain the active ingredient, suitable stabilizing agents and, if necessary, buffer substances. Antioxidizing agents such as sodium bisulfate, sodium sulfite or ascorbic acid, either alone or combined, are suitable stabilizing agents. Also used are citric acid and its salts and sodium ethylenediaminetetraacetic acid (EDTA). In addition, parenteral solutions can contain preservatives such as benzalkonium chloride, methyl- or propyl-paraben and chlorobutanol. Suitable pharmaceutical carriers are described in Remington's Pharmaceutical Sciences, a standard reference text in this field.

The active ingredients of the invention may be formulated to be suspended in a pharmaceutically acceptable composition suitable for use in mammals and in particular, in humans. Such formulations include the use of adjuvants such as muramyl dipolypeptide derivatives (MDP) or analogs that are described in U.S. Pat. Nos. 4,082,735; 4,082,736; 4,101,536; 4,185,089; 4,235,771; and 4,406,890. Other adjuvants, which are useful, include alum (Pierce Chemical Co.), lipid A, trehalose dimycolate and dimethyldioctadecylammonium bromide (DDA), Freund's adjuvant, and IL-12. Other components may include a polyoxypropylene-polyoxyethylene block polymer (Pluronic®), a non-ionic surfactant, and a metabolizable oil such as squalene (U.S. Pat. No. 4,606,918).

Additionally, standard pharmaceutical methods can be employed to control the duration of action. These are well known in the art and include control release preparations and can include appropriate macromolecules, for example polymers, polyesters, polyamino acids, polyvinyl, pyrolidone, ethylenevinylacetate, methyl cellulose, carboxymethyl cellulose or protamine sulfate. The concentration of macromolecules as well as the methods of incorporation can be adjusted in order to control release. Additionally, the agent can be incorporated into particles of polymeric materials such as polyesters, polyamino acids, hydrogels, poly (lactic acid) or ethylenevinylacetate copolymers. In addition to being incorporated, these agents can also be used to trap the compound in microcapsules.

Accordingly, the pharmaceutical composition of the present invention may be delivered via various routes and to various sites in a mammal body to achieve a particular effect (see, e.g., Rosenfeld et al., 1991; Rosenfeld et al., 1991a; Jaffe et al., supra; Berkner, supra). One skilled in the art will recognize that although more than one route can be used for administration, a particular route can provide a more immediate and more effective reaction than another route. Local or systemic delivery can be accomplished by administration comprising application or instillation of the formulation into body cavities, inhalation or insufflation of an aerosol, or by parenteral introduction, comprising intramuscular, intravenous, peritoneal, subcutaneous, intradermal, as well as topical administration. In one embodiment, delivery of the composition is aided by in vivo electroporation. In one embodiment, delivery of the composition comprises a combination of intramuscular administration and in vivo electroporation.

The active ingredients of the present invention can be provided in unit dosage form wherein each dosage unit, e.g., a teaspoonful, tablet, solution, or suppository, contains a predetermined amount of the composition, alone or in appropriate combination with other active agents. The term "unit dosage form" as used herein refers to physically discrete units suitable as unitary dosages for human and mammal subjects, each unit containing a predetermined quantity of the compositions of the present invention, alone or in combination with other active agents, calculated in an amount sufficient to produce the desired effect, in association with a pharmaceutically acceptable diluent, carrier, or vehicle, where appropriate. The specifications for the unit dosage forms of the present invention depend on the particular effect to be achieved and the particular pharmacodynamics associated with the pharmaceutical composition in the particular host.

These methods described herein are by no means all-inclusive, and further methods to suit the specific application will be apparent to the ordinary skilled artisan. Moreover, the effective amount of the compositions can be further approximated through analogy to compounds known to exert the desired effect.

EXPERIMENTAL EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Without further description, it is believed that one of ordinary skill in the art can, using the preceding description and the following illustrative examples, make and utilize the compounds of the present invention and practice the claimed methods. The following working examples therefore, specifically point out the preferred embodiments of the present invention, and are not to be construed as limiting in any way the remainder of the disclosure.

The materials and methods employed in the Examples are now described.

Plasmid Immunization and Mice

The quadriceps muscles of 6 to 8 week old female Balb/C mice (Jackson Laboratory) were injected with plasmid DNA formulations containing combinations of vector backbone (pVAX, Invitrogen), or antigenic plasmids as described (2005, Kutzler et al., J Immunol 175(1): 112-123; 1998, Kim et al., J Clin Invest 102(6) 1112-1124). Formulations contained in 0.25% bupivicaine-HCL (Sigma) in isotonic citrate buffer. Co-administration of various gene plasmids involved mixing the designated DNA plasmids so that each experimental group contains the same concentration of DNA (vector backbone added to make all groups equal DNA concentrations) before injection in a final volume of 20 µL. All DNA was made using endotoxin-free Qiagen columns. All animals were housed in a temperature-controlled, light-cycled facility at DUCOM, and their care was under the guidelines of the National Institutes of Health and IACUC/ULAR at DUCOM.

Electroporation Conditions in Mice

Square-wave pulses were used in all experiments (Draghia-Akli and Smith, 2003, In: Templeton N S, Lasic D D (eds.) Gene Therapy—Therapeutic Mechanisms and Strategies. Marcel Dekker, Inc., New York, 245-263) and delivered with the constant-current EKD that was designed and tested in our laboratory. A three electrode array (3-EA) was used in the mouse experiments. The 3-EA consists of three 26-gauge solid stainless steel electrodes in an isosceles triangle formation, with the two long sides 0.5 mm in length and short side 0.3 mm in length, held together with a nonconductive plastic. Specific EP conditions for the mouse experiments were using constant current, 0.1 Amps, three pulses, 52 msec/pulse, 4 sec between pulses. The lag time between plasmid injection and EP was about 20 sec. The sequence of events for plasmid administration/EP was as follows: Place a disposable electrode assembly in the receptacle of the handle, press initiation button on handle and enter animal experimental group number, inject DNA construct plasmid using insulin syringe, immediately place needles into area surrounding the injection site, press initiation button on handle, and after 4 second countdown, pulses will be delivered. After 5 seconds following electroporation, the array is gently removed from muscle. All electrodes were completely inserted into the muscle during all treatments.

Method for Mouse Sacrifice, Tissue or Sample Harvest and Cell Purification for Immune Analysis At endpoints designated in the legends, the animals were sedated using avertin or isofluorane and appropriate amounts of blood and fecal pellets were taken prior to animal sacrifice. Following sacrifice, the spleen from each mouse were harvested from each experimental group and tissue was placed into a 15 mL conical tube containing R10 medium (RPMI1640 plus 10% fetal bovine serum, 500 µg/L penicillin, and 500 µg/L streptomycin, Gibco, Invitrogen). The spleens from each experimental group were crushed into a single cell suspension using a Seward Stomacher 80, put through a 40 micron cell strainer, washed with medium, pelleted and incubated for 5 to 10 minutes at room temperature in ACK lysing buffer resulting in the lysis of red blood cells. All cells were washed, resuspended in medium, and counted (cell viability is determined using trypan blue stain) using a hemacytometer.

Analysis of IgG and IgA Binding Antibodies by ELISA

ELISA was used to determine antigen-specific IgG in mouse serum and fecal extract as described (1989, Ogawa et al., J Immunol 142(4): 1150-1158; 2004, Mestecky et al., AIDS research and human retroviruses 20(9): 972-988). Mouse blood samples were harvested from mice by submandibular or retroorbital bleeds and fecal pellets were obtained from the cage of mouse groups, and subsequently, both serum and fecal samples were run individually within each experimental group. EIA/RIA plates (Costar) were coated with 0.5 to 2 mg/mL of Toxoid A or B (List Biologicals) diluted in PBS (Mediatech) at a final volume of 100 µL per well and incubated overnight at 4° C. Plates were washed with PBS/Tween (0.05% Tween 20) three times and blocked against non-specific binding with 200 µL of blocking buffer/diluent (3% BSA in PBS) for 2 hours at room temperature. The plates were washed and pooled sera or fecal extract from immunized mice diluted in PBS/1% BSA was added to wells at a final volume of 100 µL. Samples were added in triplicate, at dilutions from 1 to 25 to 1 to 150,000 dilution series to determine endpoint titer (defined as the lowest sample dilution at which measurements for experimental group are equal to vector-immunized mouse sample O.D. values) and incubated at room temperature for 2 hours or overnight at 4° C. Bound antibodies were detected with horseradish peroxidase-labeled goat anti-mouse IgG or IgA (Santa Cruz) and developed with substrate TMB $H_2O_2$ (SIGMA). The color reaction was stopped with 2N $H_2SO_4$, and the absorbance at 450 nm was read in an EL312 Bio-Kinetics microplate reader (Bio-Tek Instruments Inc.). The amount of total IgG or IgA in sera or fecal secretions was calculated by interpolating the optical densities on calibration curves, using the DeltaSoft II program (BioMettalics, Inc.).

B Cell ELISPOT for Measurement of IgA and IgG

B cell ELISPOT was carried out as described previously (1996, Slifka et al., J Immunol Met 199(1): 37-46; 2000, Brown et al., J Infect Dis 182(4): 1039-1043; 2004, Crotty et al., J Immunol Met 286(1-2): 111-122; 2003, Qadri et al., Infect Immun 71(8): 4808-4814) with some modifications as described below. Immunized mice were sacrificed one week following the last immunization and antibody-secreting cells were harvested from splenocytes. ELISpot 96-well plates were coated with 2 µg/mL of Toxoid A or B (List Biologicals) diluted in PBS (Mediatech) at a final volume of 100 µL per well, and incubated for 24 hours at 4° C. The plates were washed and blocked for 2 hours with 1% BSA. Five hundred thousand total lymphocytes from the immunized mice were added to each well in triplicate and incubated for 5 hours at 37° C., 5% $CO_2$. The plates were washed and 100 µL of a 1:2000 dilution of anti-mouse IgA-biotin (diluted in PBS/1% BSA) was added and incubated overnight at 4° C. The plate was washed, and 100 µL of 1:100 dilution of streptavidin-alkaline phosphatase (diluted in PBS/1% BSA) was added and incubated for 2 hours at room temperature. The plates were washed and (BCIP) and (NBT) substrates were added to each well. The plate was rinsed with distilled water, and dried at room temperature. Spots were counted by an automated ELISpot reader (CTL Limited, Inc.) and by eye. Raw values are determined and multiplied by a factor so that data is represented as ASC (antibody-secreting cells) per million IgA-secreting B cells.

Statistical Analysis

Data are presented as the mean±standard deviation (st dev) calculated from triplicate wells of pooled lymphocytes from each experimental group. Where appropriate, the statistical difference between immunization groups was assessed by using a two-tailed, paired Student's t Test and yielded a specific p value for each experimental group. Comparisons between samples with a p value <0.05 were considered to be statistically different and therefore significant.

The results of the experiments are now described.

Example 1

Figure 1B:
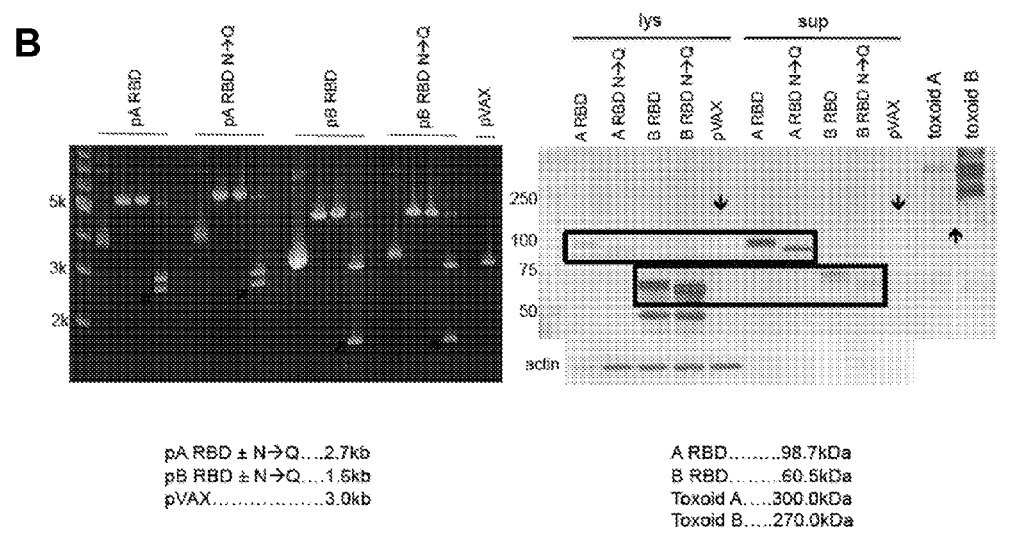

Development of an Optimized DNA-Based Vaccine that Encodes Toxin A and Toxin B Receptor Binding Domains of C. difficile Delivered Through Intramuscular Route Followed by Electrostimulation Construction and Expression of C. difficile RBD Plasmids Highly optimized plasmids were designed based on the toxin A (TcdA) and toxin B (TcdB) of C. difficile in combination with novel plasmid-based mucosal chemokines. For generation of highly optimized antigenic constructs, the full-length amino acid sequence corresponding to the Toxin A and B proteins of C. difficile strain VPI 10463 (NCBI AAA23283) were identified; the residues corresponding to the amino-acid sequence of the putative receptor-binding domain (RBD) known to occupy the carboxy-terminal third of the protein was back-translated in silico to a novel genetic sequence. Gene modifications were introduced to enhance protein expression including codon optimization (for human), addition of an effective secretory leader (IgE), KOZAK context, and removal of cis-acting sequence motifs/RNA secondary structures that impede translation (FIG. 1). In addition, potential N-linked glycosylation sequences were mutated to protect the native glycosylation of the bacterial toxins. This gene was then submitted for commercial synthesis (Geneart). The gene insert was digested (EcoRI/XhoI, New England Biolabs) and ligated into the commercial vector, pVAX (Invitrogen, Carlsbad, Calif.), and protein expression was confirmed by western blot for testing in vivo (FIG. 1). The antigenic constructs are termed TcdA-RBD and TcdB-RBD. Taken together, these data demonstrate that the plasmid forms of the chemokines express the specific chemokine protein.

Immunization Induced In Vivo Production of TcdA- and TcdB-Specific Antibodies and Antibody Secreting Cells (ASCs)

Figure 2:
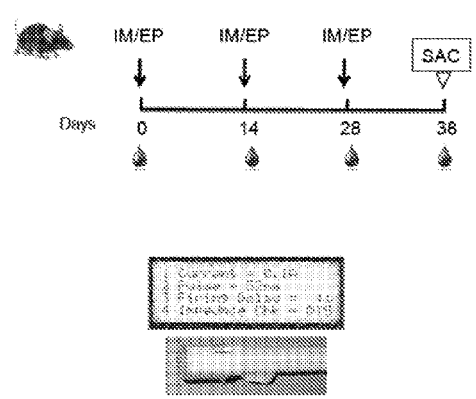
FIG. 2 depicts the results of experiments demonstrating that toxin-specific IgG, but not IgA, is detectable in the sera of mice immunized intramuscularly followed by in vivo electroporation.
Figure 2:
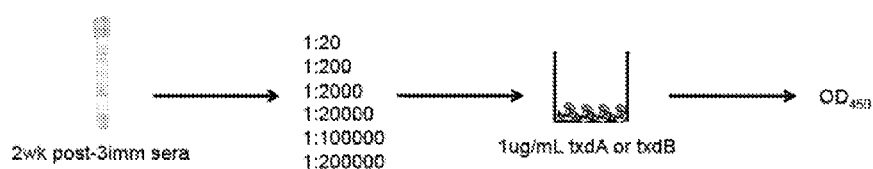
Figure 2:
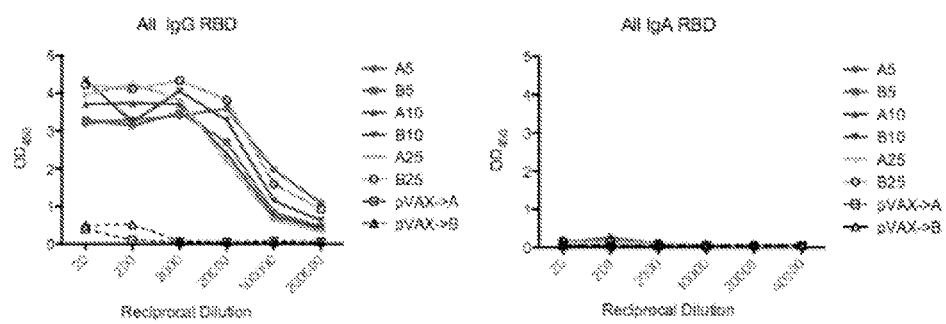

Female Balb/C mice (6 to 8 weeks old) were immunized with plasmid DNA formulations for varied quantities of antigenic constructs (5 µg, 10 µg, or 25 µg) of either pA RBD N→Q or pB RBD N→Q, along with requisite amount of inert vector backbone, pVAX, to ensure a total 25 µg of total plasmid. Mice were immunized at day 0, day 14, and day 28. Mice were sacrificed at day 38. Sera and fecal samples from immunized groups were diluted in PBS/1% BSA at dilutions ranging from 1:20 to 1:200000. Dilutions were applied to EIA/RIA plates which had been coated with 1 µg/mL toxoid A (txdA) or toxoid B (txdB). Following incubation, antibody binding was detected through the absorbance read at 450 nm (OD450). Antibody binding was detected for all quantities of pA RBD N→Q and pB RBD N→Q tested (FIG. 2). Further, toxin A and toxin B specific IgG, but not IgA, was detected in the sera of the immunized mice.

Figure 3:
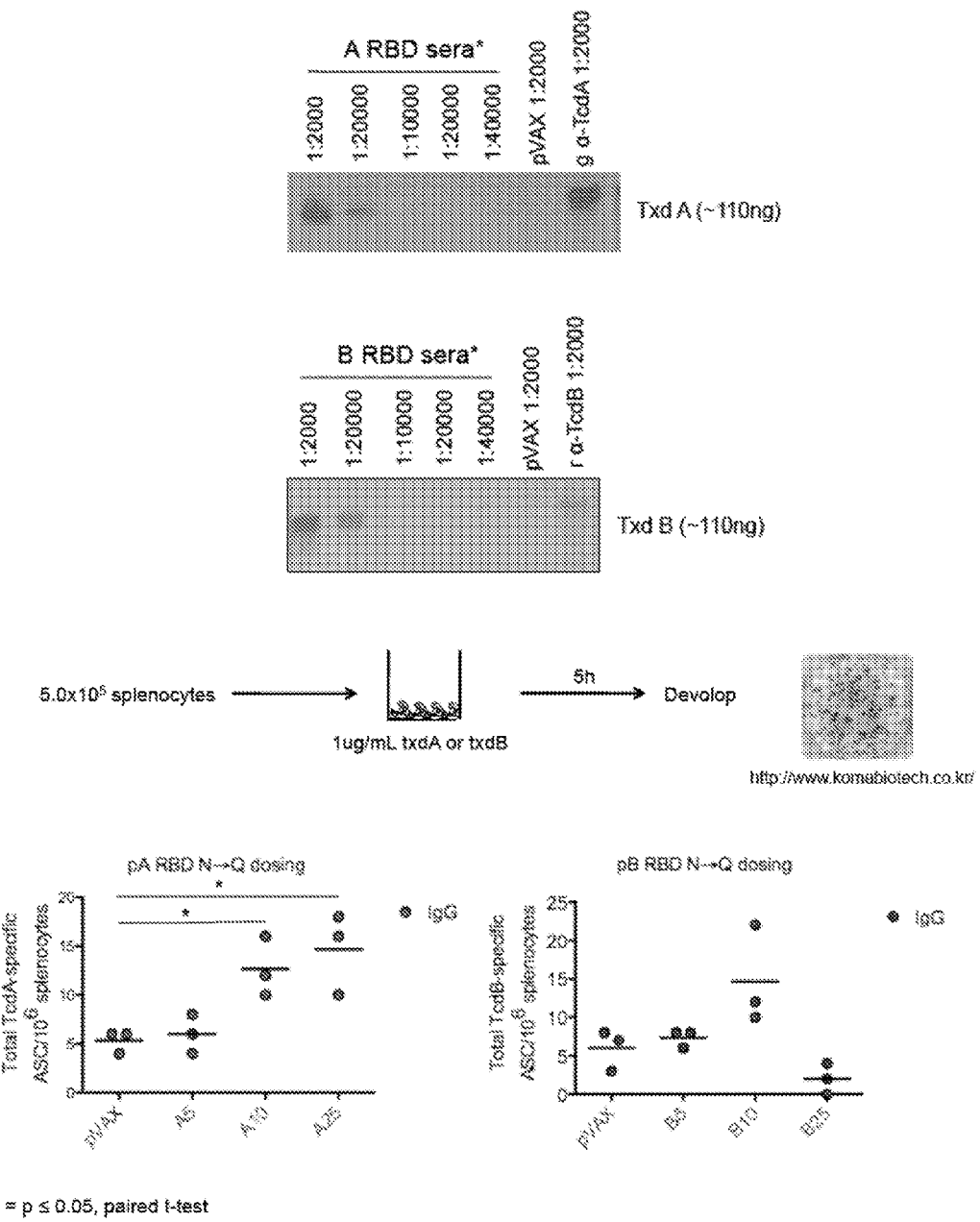
FIG. 3 depicts the results of experiments assessing the number of toxin A- and toxin B-specific antibody secreting cells after pA/B RBD N→Q dosing in mice.

Spleens were harvested one week following immunization and ASCs were harvested from splenocytes as described elsewhere herein. B cell ELISPOT assays were carried out using ELISPOT 96-well plates that were coated with 2 µg/mL of txdA or txdB. Counted spots after incubation with cells from immunized groups demonstrate that immunization with pA RBD N→Q or pB RBD N→Q produced increased numbers of ASCs in immunized mice (FIG. 3).

Concurrent immunization with TcdA-RBD and TcdB-RBD

Figure 4:
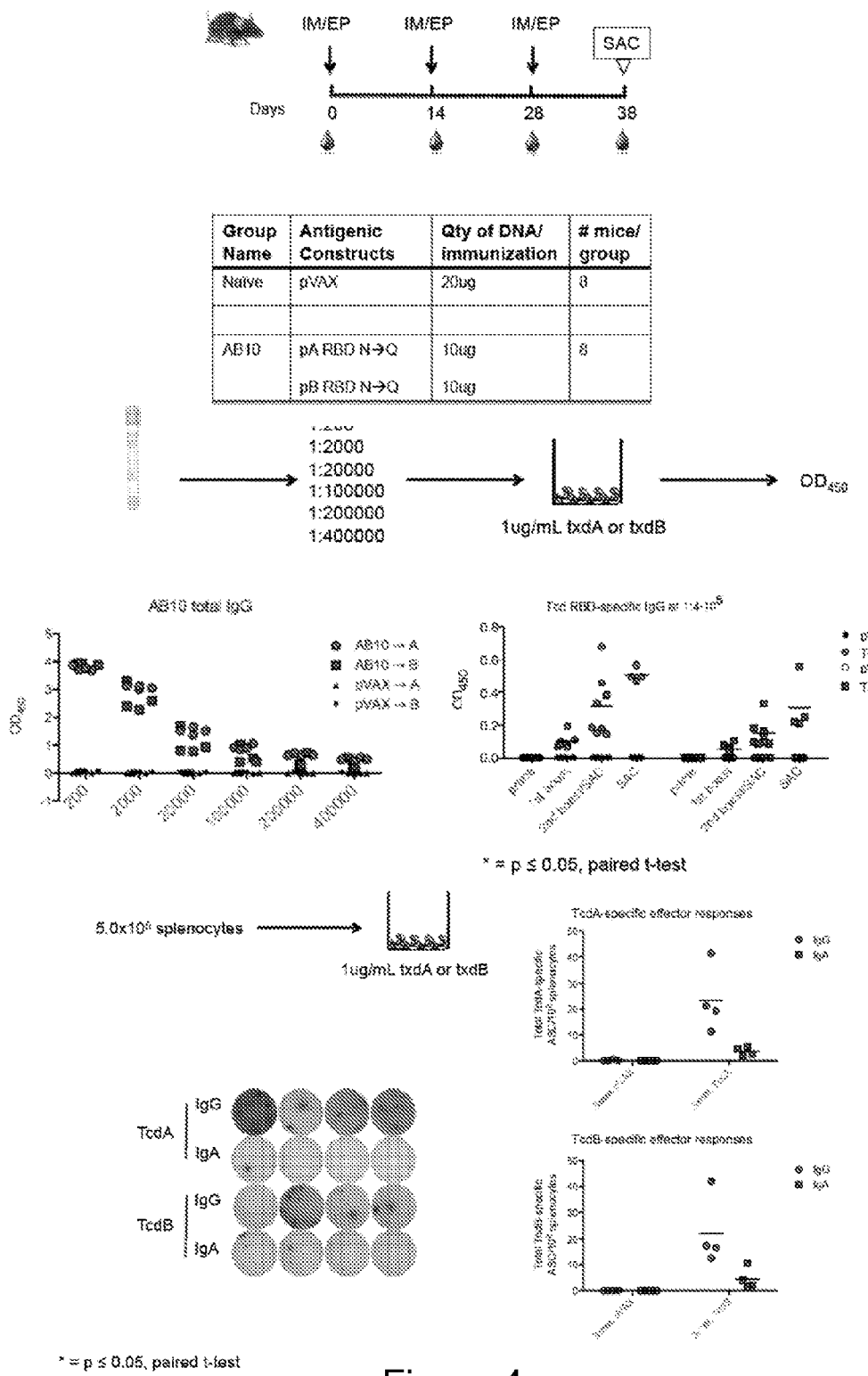
FIG. 4 depicts the results of experiments demonstrating that toxin-specific plasmablasts are augmented in the spleens of pRBD-immunized mice.
Figure 5:
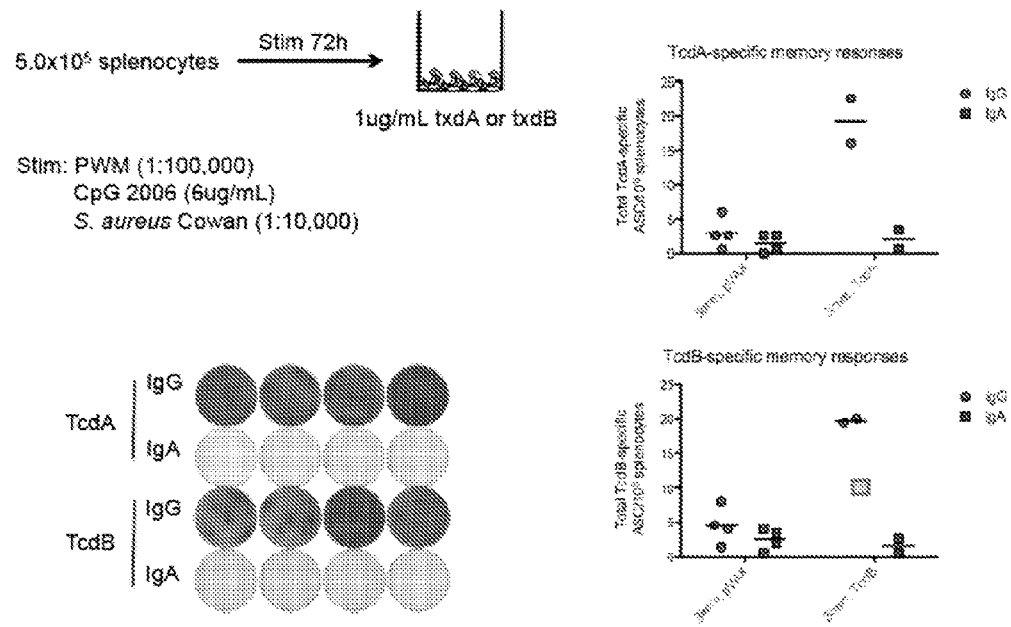
FIG. 5 depicts the results of experiments analyzing the phenotype of vaccine-induced B cells, and of experiments demonstrating that toxin-specific memory responses are augmented in the spleens of pRBD-immunized.
Figure 5:
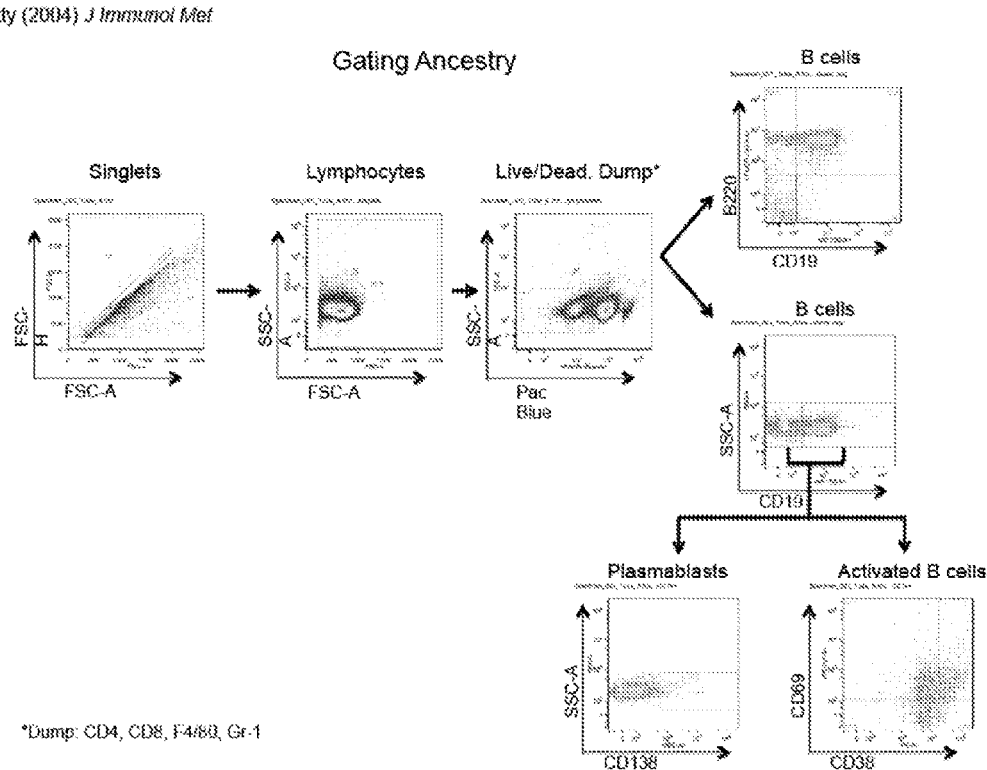

Mice were immunized by IM/EP at day 0, day 14, and day 28 with 10 ug pA RBD N→Q and 10 µg pB RBD N→Q concurrently, or with 20 µg of vector backbone control, pVAX. Toxin A and toxin B specific antibodies were detected by ELISA in sera samples of immunized animals (FIG. 4). Further, isolated splenocytes from immunized animals demonstrate increased counts of both toxin A-specific and toxin B-specific ASCs following immunization (FIG. 4).

Toxin Specific Memory Responses and Analysis of Vaccine-Induced B Cells

Splenocytes from vaccinated mice were stimulated for 72 hours with PWIM (1:100,000), CpG 2006 (6 µg/mL), and S. aureus Cowan (1:10,000), and were then incubated with plates coated with 1 µg/mL txdA or txdB. Toxin A-specific and toxin B-specific memory responses were observed, as stimulated splenocytes harvested from toxin A- or toxin B-vaccinated mice displayed increased number of toxin A- or toxin B-specific ASCs.

Sera from RBD-Immunized Animals Prevents Cell Rounding

Figure 6:
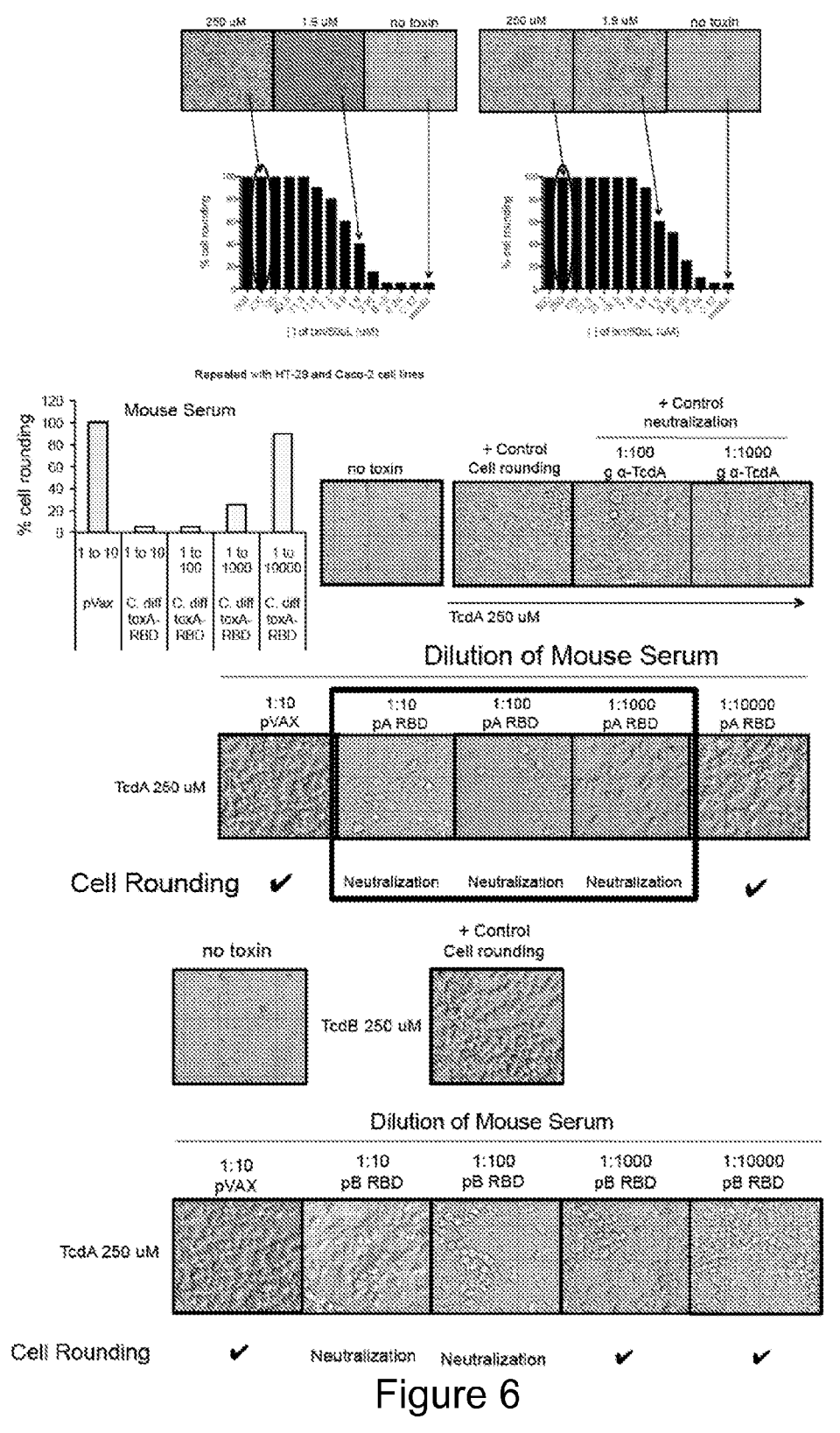

Application of toxin results in the dose-dependent rounding of Vero cells, an immortalized cell line derived from kidney cells from the African green monkey. Thus, cell rounding can be used as a marker of toxin-mediated pathology in vitro. Serum samples from mice immunized with pA RBD N→Q displayed the ability to prevent cell rounding that is induced from 250 ng toxin A. Further, serum samples from mice immunized with pB RBD N→Q also demonstrated the ability to prevent rounding of cells seen with application of 250 ng toxin B (FIG. 6). Together, these data show that toxin A- and toxin B-specific antibodies produced in mice immunized with the DNA constructs described herein protect against the pathology induced by the toxins generated by C. difficile.

IM/EP Immunization with pCdiffA/B Protects Mice from System Toxic Challenge

Figure 7:
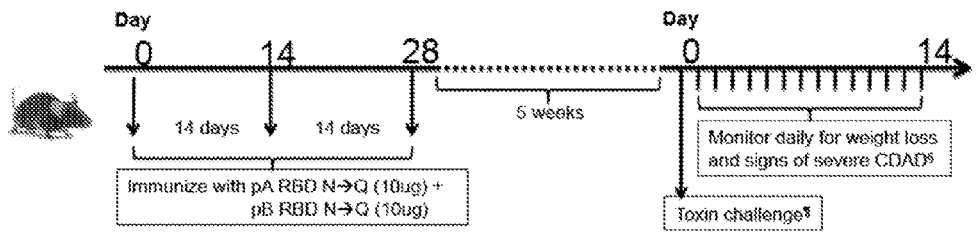
FIG. 7 depicts the results of experiments demonstrating that immunization with pRBD N→Q protects mice from systemic toxin challenge.
Figure 7:
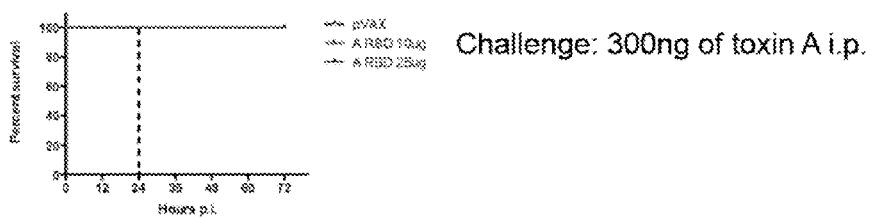
Figure 7:
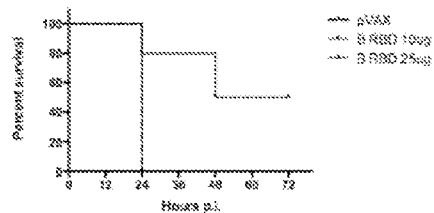

Mice were immunized on days 0, 14, and 28 with pA RBD N→Q and pB RBD N→Q. Five weeks after the final immunization dose, mice were challenged with toxin A and toxin B. Mice were then monitored daily for 14 days for weight loss and signs of C. difficile-associated disease (CDAD). In mice immunized with only the control pVAX, all challenged mice died within 24 hours. However mice immunized with 25 µg pA RBD N→Q were protected against death mediated by 300 ng of toxin A, while mice immunized with 25 µg pB RBD N→Q were protected against death mediated by the challenge of 150 ng of each toxin A and toxin B (FIG. 7).

Immunization of Female Indian Rhesus Macaques

Figure 8:
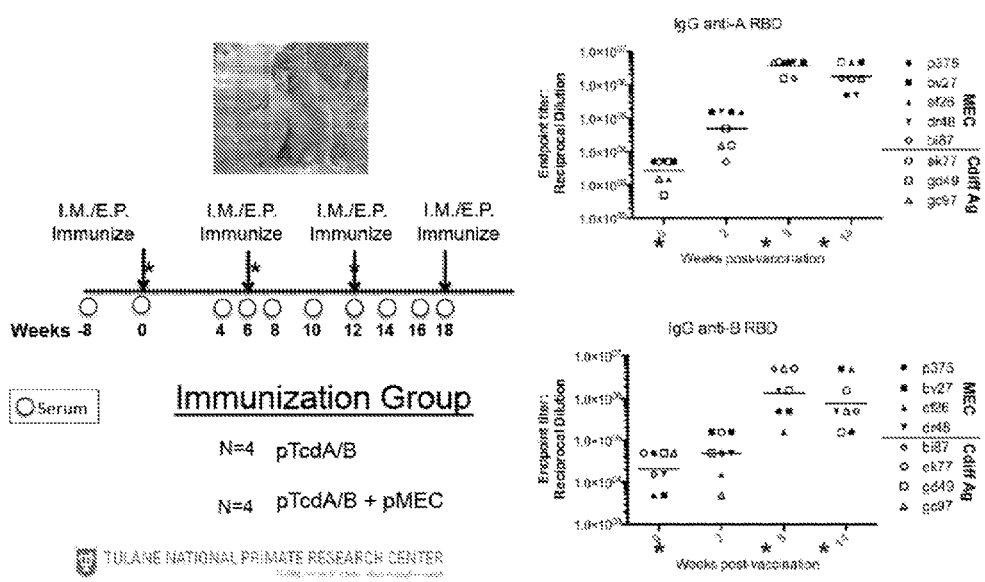
FIG. 8 depicts the immunization schedule and immunogenicity observed in female Rhesus macaque after intramuscular immunization and in vivo electroporation.

Female Indian rhesus macaques were immunized by IM/EP at weeks 0, 6, 12, and 18 with either pTcdA/B N→Q. Titers of IgG anti-A RBD and IgG anti-B RBD were evaluated at weeks 2, 8, and 14. Analysis demonstrated that the vaccinated constructs were highly immunogenic, as specific antibodies were detected throughout the immunization schedule. (FIG. 8)

Example 2

Development of a Novel DNA Vaccine for the Prevention of CDAD

Figure 9A:
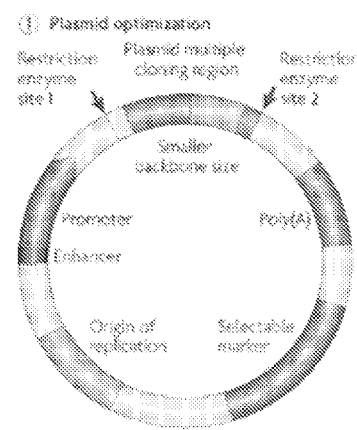
Figures 9D, 9E:
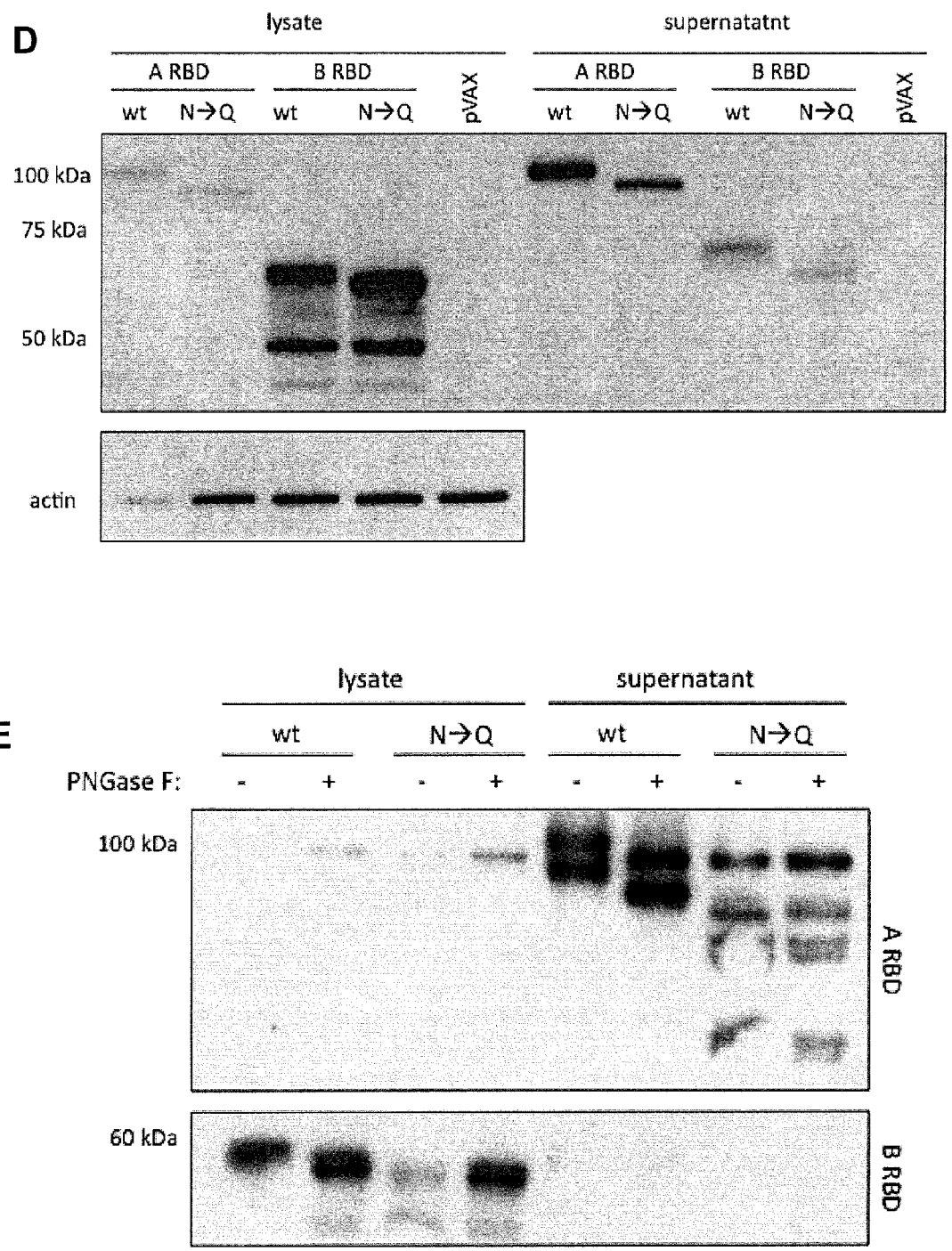

Described herein is the creation of highly optimized plasmids encoding RBD from toxin A and toxin B, where putative N-linked glycosylation sites were altered. Antigen DNA modifications included herein are summarized in FIG. 9A. A plasmid map displaying key components of pVAX is shown in FIG. 9A. Four plasmids, encoding A or B RBD wt and A or B RBD N→Q were optimized and constructed. Putative N-linked glycosylation sites in the RBD of toxins A and B are underlined as shown in FIG. 9B. At these sites, Gln (Q) was substituted for the first Asn (N) during construction of the DNA vaccine plasmids. To verify expression, 293T cells ($3.0 \times 10^5$ cells) were transfected with 2 µg of pRBD N→Q constructs using Lipofectamine 2000. Forty-eight hours post-transfection, lysates (RIPA buffer) and supernatants were harvested, fractionated on SDS-PAGE (4-12%), and transferred to PVDF membrane. Immunodetection was performed with specific mouse antiserum and the expressed proteins were visualized with horseradish peroxidase-conjugated goat anti-mouse IgG using an ECL detection system (FIG. 9C). Aliquots of lysates and supernatants were digested with 500 U of polypeptide N-glycosidase F (PNGaseF) for 1 hour at 37° C. and deactivated at 65° C. for 15 minutes. Samples were subjected to SDS-PAGE (8%) and immunodetection as described above (FIG. 9D). Immunodetection of the constructs demonstrated that the N→Q constructs were not glycosylated.

Figure 10:
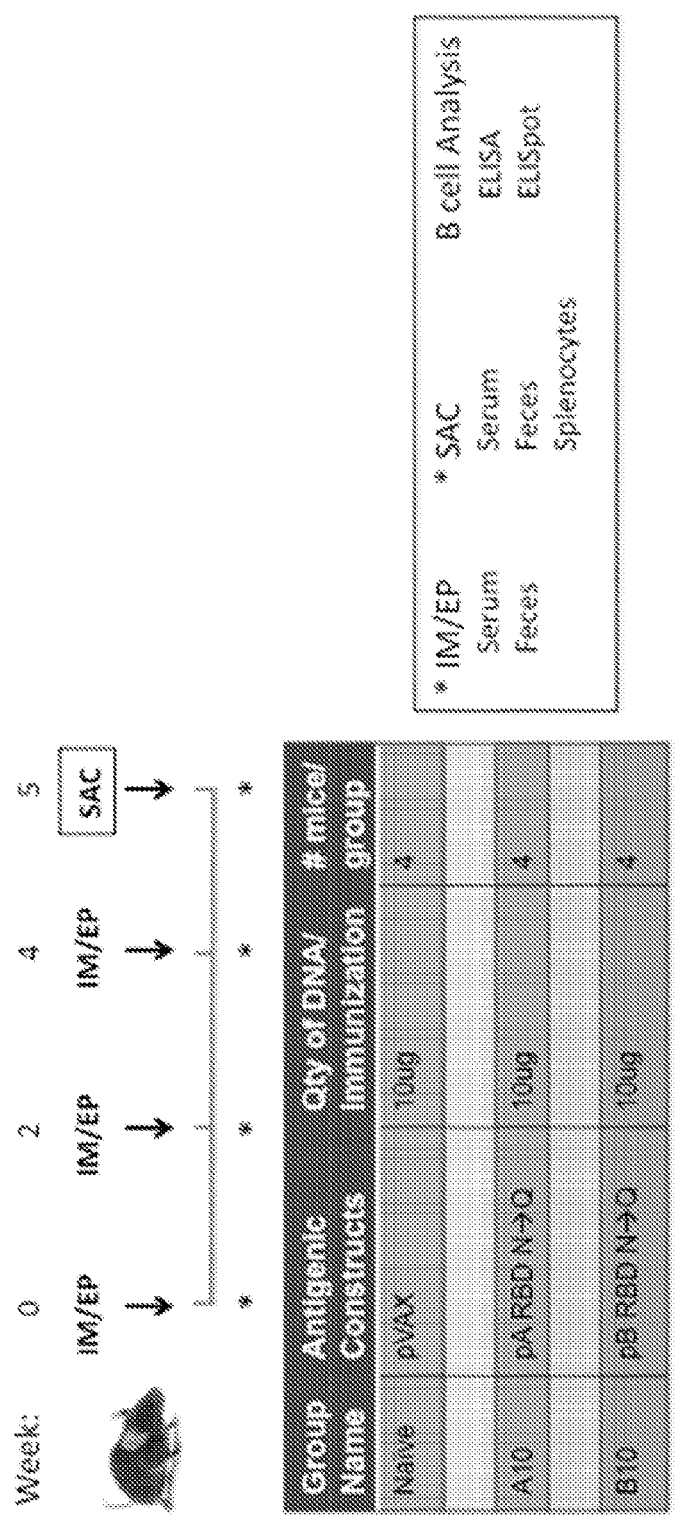
FIG. 10 depicts an immunization and collection schedule.
Figure 11A:
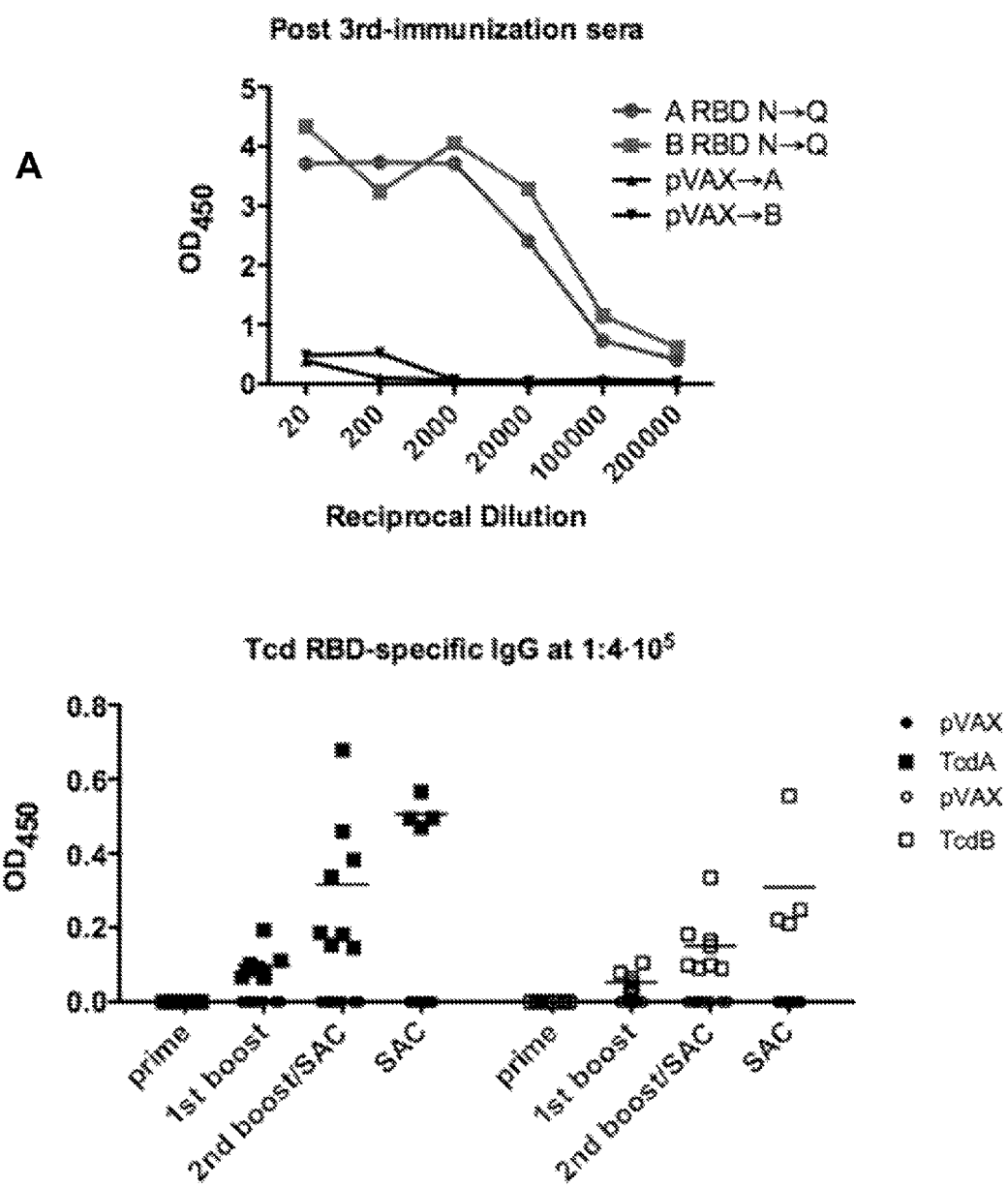
FIGS. 11A-11C depicts the results of experiments assessing antigen-specific B cells after immunization with pRBD N→Q. (A) Antibody levels were measured in sera at the time of each immunization. 96-well plates were coated overnight with 0.5 μg/mL of either toxoid A or B. Dilutions of sera were added, and total IgG was measured using HRP-conjugated antibodies. (B) ELISpot plates were coated overnight with 0.5 μg/mL of either toxoids A or B or total IgG. Splenocytes were isolated 10 days post third immunization and added to the plate (Ag-specific, $5.0 \times 10^5$ cells/well and total IgG, $1.0 \times 10^4$ cells/well). After 24 hours, cells were washed off and probed with HRP-conjugated antibodies. (C) Alternatively, splenocytes ($1.5 \times 10^6$) were stimulated for 3 days in R10 media plus 1:6 CpG2006, 1:1000 PWM, 1:1000 BMe, and 1:10000 SAC to encourage memory B cells to proliferate. Antigen-specific memory B cells were detected, as described elsewhere herein.

C57BL/6 mice (n=4/group) were immunized intramuscularly 3 times with both plasmids, 2 weeks apart, followed by in vivo electroporation (FIG. 10). Sera and fecal matter were collected longitudinally and analyzed for Tcd A/B RBD-specific immune responses. Antibody levels were measured in sera at the time of each immunization. 96-well plates were coated overnight with 0.5 µg/mL of either toxoid A or B. Dilutions of sera were added, and total IgG was measured using HRP-conjugated antibodies (FIG. 11A). Analysis of sera demonstrated that vaccination induced significant levels of anti-RBD antibodies.

Figures 11B, 11C:
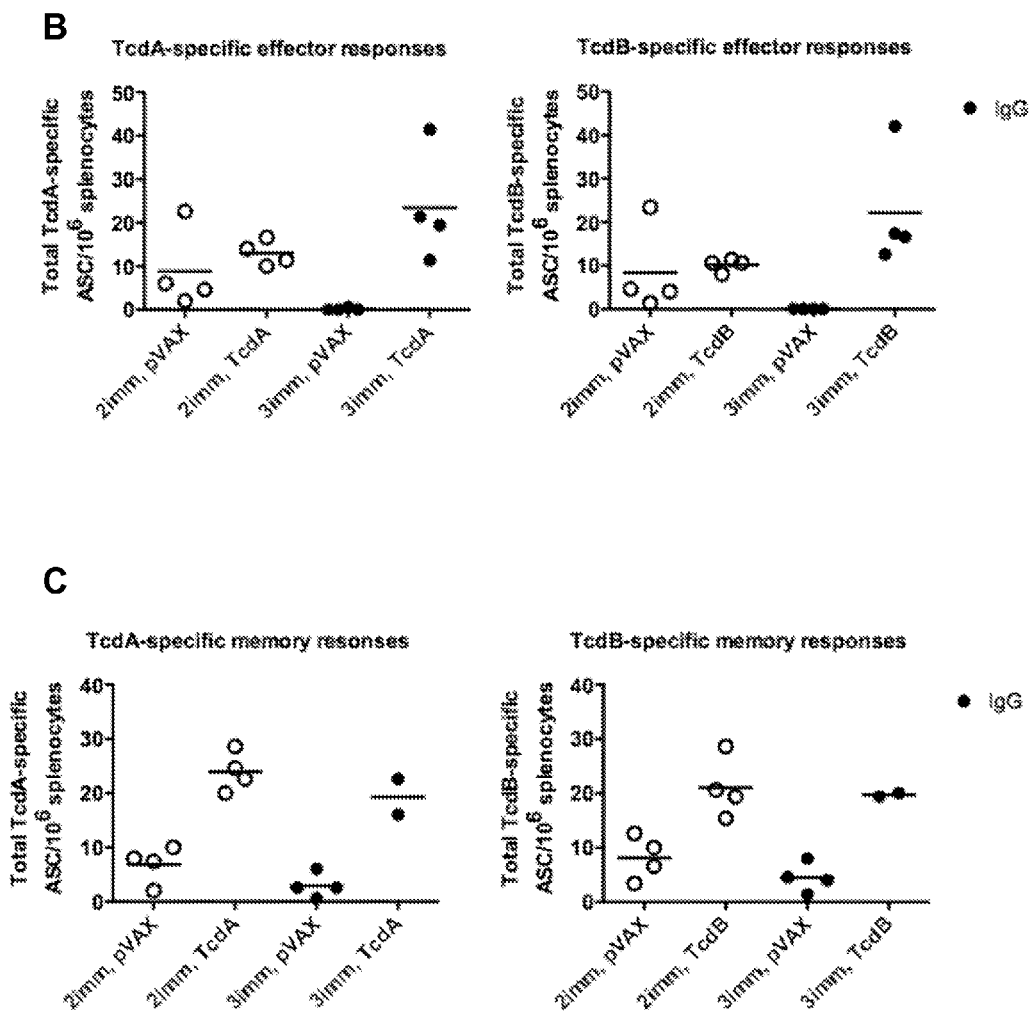

ELISpot plates were coated overnight with 0.5 µg/mL of either toxoids A or B or total IgG. Splenocytes were isolated 10 days post third immunization and added to the plate (Ag-specific, $5.0 \times 10^5$ cells/well and total IgG, $1.0 \times 10^4$ cells/well). After 24 hours, cells were washed off and probed with HRP-conjugated antibodies (FIG. 11B). Alternatively, splenocytes ($1.5 \times 10^6$) were stimulated for 3 days in R10 media plus 1:6 CpG2006, 1:1000 PWM, 1:1000 BMe, and 1:10000 SAC to encourage memory B cells to proliferate (FIG. 11C). Antigen-specific memory B cells were detected as described above. Analysis of splenocytes demonstrated that vaccination elicited increased frequency of RBD-specific antibody secreting cells. Further, splenocytes from vaccinated mice demonstrated increased RBD-specific memory responses. Additionally, peripheral titers of antigen-specific IgG were higher than IgA.

Figure 12A:
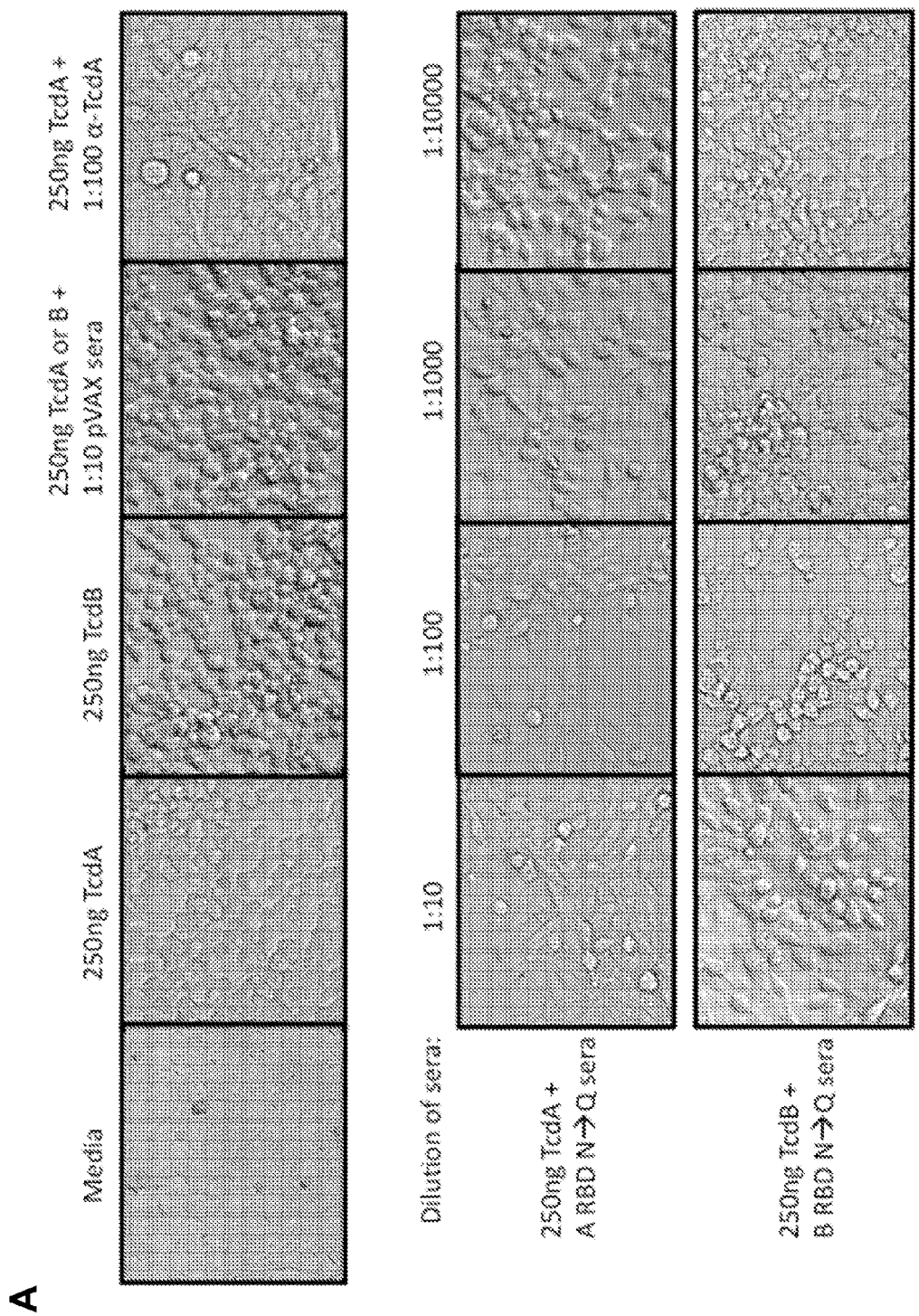

Vero cells ($5.0 \times 10^4$ cells) were grown to a monolayer (24 hours) in a 96-well plate. Mouse sera was diluted in 25 µL of R10 media and added to 25 µL of R10 containing 250 ng of either toxin A or toxin B. This was mixed gently, incubated for 1 hour at 37° C. and added in duplicate to the 96-well plate. After 20-24 hours, cell rounding was assessed under 10× magnification. Pictures represent the average effect across two wells. Goat anti-toxin A (List Biologicals) was used as a positive control (FIG. 12A). Sera from pRBD N→Q immunized mice neutralized the cytopathic effects of *C. difficile* toxin in vitro. Quantification of cell rounding was performed by analyzing 6 random fields per well and averaging the percentage of rounded cells. Results were graphed in comparison to pVAX sera and goat anti-toxin A (FIG. 12B). This data demonstrates that RBD A N→Q sera neutralized toxin activity more effectively than RBD B N→Q sera.

Figure 13:
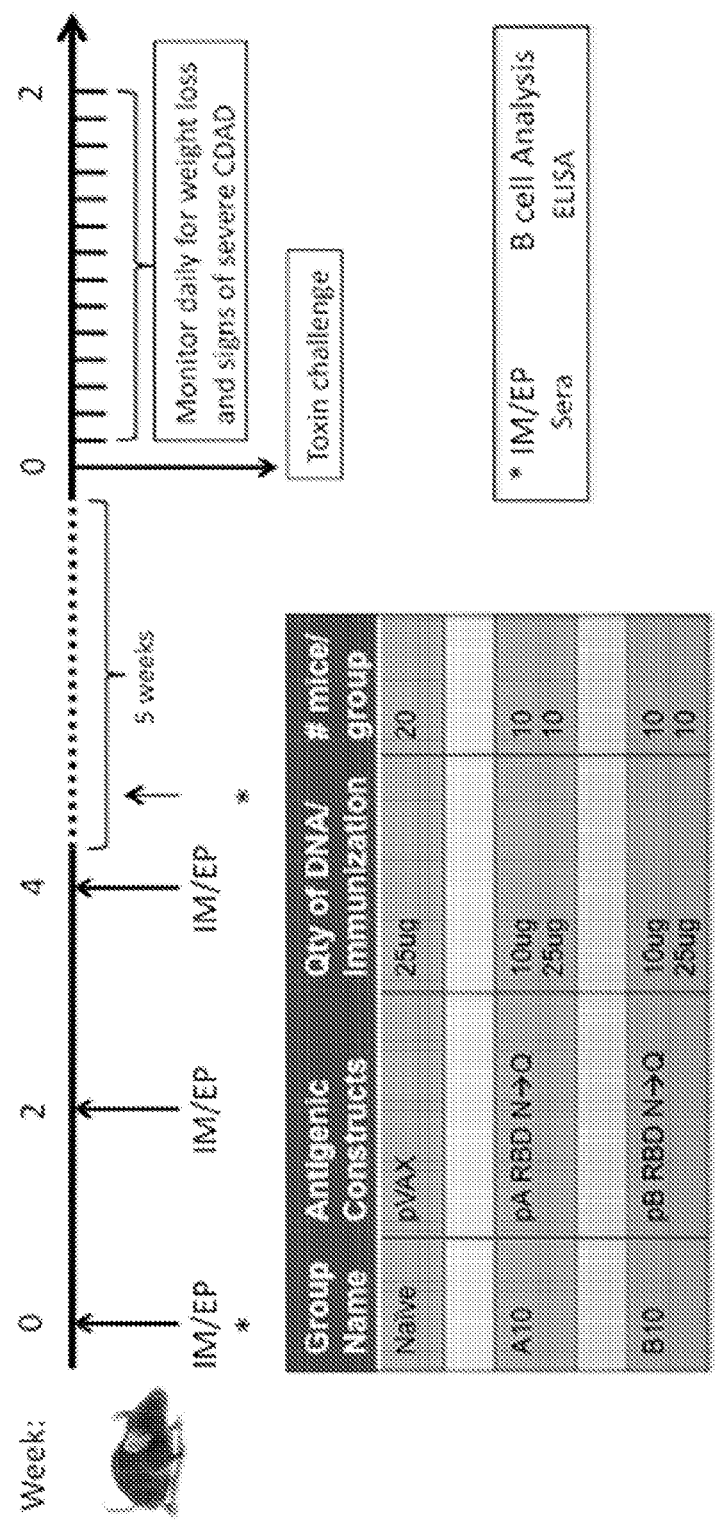
FIG. 13 depicts an immunization and collection schedule.
Figure 14:
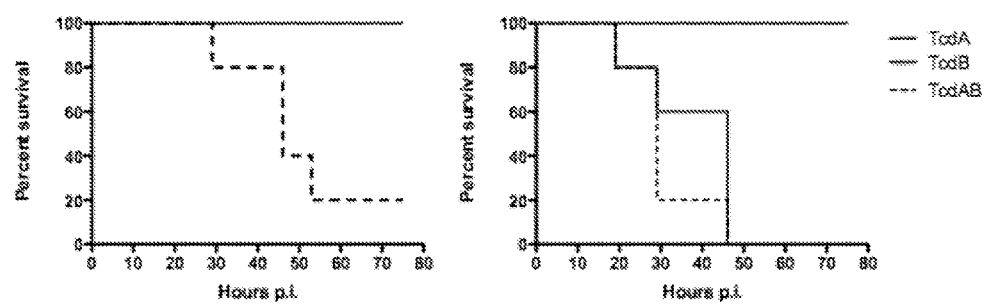
FIG. 14 depicts the results of experiments assessing lethal systemic challenge with purified C. difficile toxins. (A) Five C57BL/6 mice were challenged intraperitoneally (i.p.) with either (1) 150 ng toxin A or B; (2) 300 ng toxin A or B; (3) 75 ng of both toxins; or (4) 150 ng of both toxins. Mice were monitored daily for signs of morbidity. (B) 10 C57BL/6 mice/group were challenged i.p. with toxin. pA RBD N→Q mice received 300 ng Toxin A, while pB RBD N→Q mice received 150 ng of each toxin.
Figure 14:
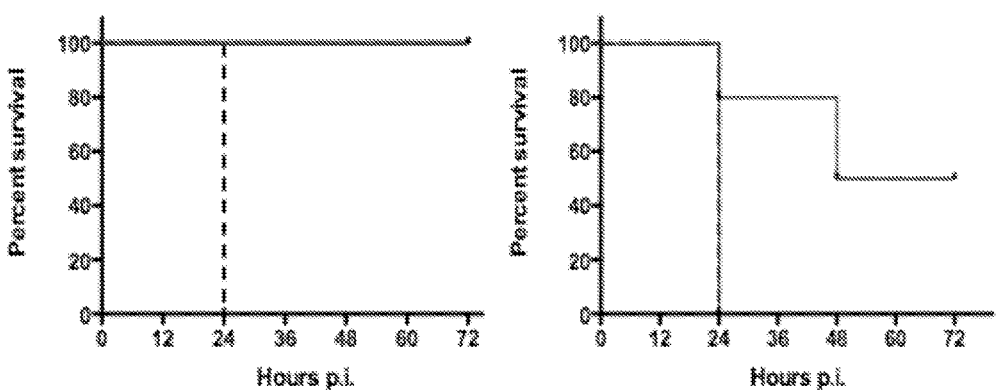
Figure 15:
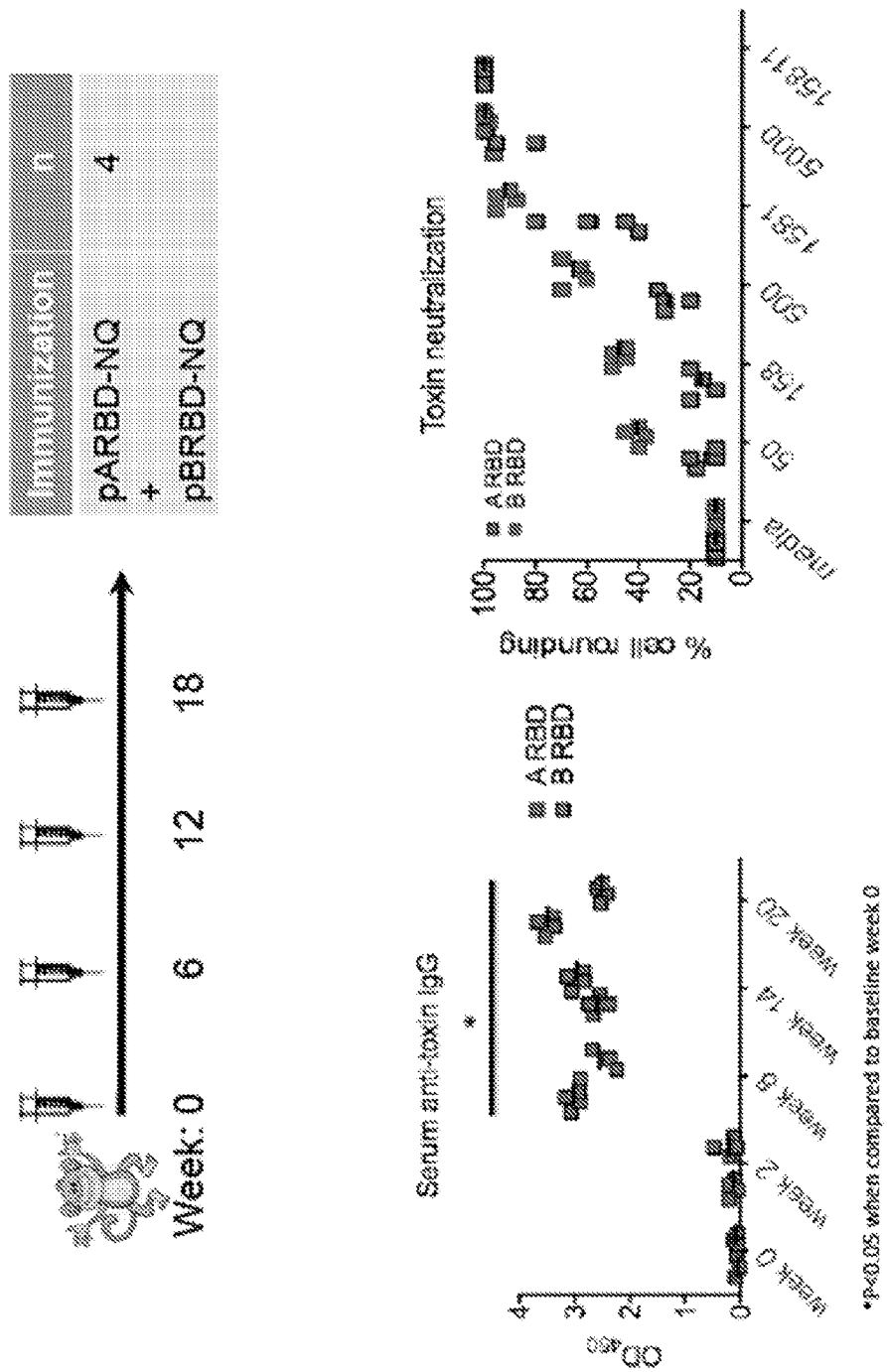
FIG. 15 depicts the results of experiments demonstrating that pRBD-N→Q constructs are immunogenic in Rhesus macaques.

The ability for toxin specific vaccinations to respond to lethal toxin challenges was assessed in a mouse model. Mice were immunized at week 0, 2, and 4. After 5 weeks post immunization, mice were challenged with toxin and monitored for 2 weeks (FIG. 13). Five C57BL/6 mice were challenged i.p. with either (1) 150 ng toxin A or B; (2) 300 ng toxin A or B; (3) 75 ng of both toxins; or (4) 150 ng of both toxins. Mice were monitored daily for signs of morbidity (FIG. 14A). It was observed that 300 ng of toxin A and 150 ng of each toxin A and Tcd B resulted in the death of all challenged animals within 50 hours. Ten C57BL/6 mice/group were challenged i.p. with toxin. A RBD N→Q mice received 300 ng toxin A, while B RBD N→Q mice received 150 ng of each toxin (FIG. 14B). It was observed that vaccination significantly improved survival.

These data demonstrate the robust immunogenicity of a toxin A/B RBD-based DNA vaccine. It is seen that optimized plasmids containing disrupted N-linked glycoslyation sites can be expressed in a mammalian cell line. Wild-type RBD expressed by 293T cells is glycosylated unlike N→Q RBD, demonstrating that the mutations are necessary to preserve the non-glycosylated forms of the native *C. difficile* RBD regions.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A vaccine comprising at least one nucleic acid selected from the group consisting of:
   a. a nucleic acid encoding a polypeptide comprising the amino acid sequence of SEQ ID NO:3; and
   b. a nucleic acid encoding a polypeptide comprising the amino acid sequence of SEQ ID NO:4.

2. The vaccine of claim 1, further comprising a nucleic acid encoding a secretory leader peptide.

3. The vaccine of claim 2, wherein the secretory leader peptide is an IgE secretory leader peptide.

4. The vaccine of claim 1, wherein the nucleic acid is incorporated into one expression vector.

5. The vaccine of claim 1, wherein the nucleic acid is incorporated into two or more expression vectors.

6. The vaccine of claim 1, wherein the at least one nucleic acid is codon-optimized for expression in a human cell.

7. An isolated nucleic acid encoding the amino acid sequence selected from the group consisting of SEQ ID NO:3 and SEQ ID NO:4.

8. A composition comprising an isolated nucleic acid encoding the amino acid sequence of SEQ ID NO:3 and an isolated nucleic acid encoding the amino acid sequence of SEQ ID NO:4.

* * * * *